United States Patent
Huang et al.

(10) Patent No.: US 12,337,114 B2
(45) Date of Patent: Jun. 24, 2025

(54) BREATHING APPARATUS WITH MASK ASSEMBLY FOR DELIVERING BREATHING GASES

(71) Applicant: Fisher & Paykel Healthcare Limited, Auckland (NZ)

(72) Inventors: Wen Dong Huang, Auckland (NZ); Arvin San Jose Gardiola, Auckland (NZ); Matthew Roger Stephenson, London (GB); Toong Chuo Lim, Auckland (NZ); Bruce Michael Walls, Auckland (NZ); Jeremy Owen Young, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 696 days.

(21) Appl. No.: 17/447,757

(22) Filed: Sep. 15, 2021

(65) Prior Publication Data
US 2022/0001127 A1 Jan. 6, 2022

Related U.S. Application Data

(63) Continuation of application No. 15/524,802, filed as application No. PCT/NZ2015/050186 on Nov. 6, 2015, now Pat. No. 11,154,681.
(Continued)

(51) Int. Cl.
*A61M 16/06* (2006.01)
*A61M 16/08* (2006.01)
(Continued)

(52) U.S. Cl.
CPC .... *A61M 16/0683* (2013.01); *A61M 16/0622* (2014.02); *A61M 16/0666* (2013.01);
(Continued)

(58) Field of Classification Search
CPC .............. A61M 16/06; A61M 16/0605; A61M 16/0661; A61M 16/0683; A61M 16/0611;
(Continued)

(56) References Cited

U.S. PATENT DOCUMENTS

| 2,641,018 A | 6/1953 | Snyder |
| 4,501,027 A | 2/1985 | Olsson |

(Continued)

FOREIGN PATENT DOCUMENTS

| CN | 2334884 Y | 8/1999 |
| CN | 1623610 A | 6/2005 |

(Continued)

*Primary Examiner* — Bradley H Philips
*Assistant Examiner* — Savannah L Gabriel
(74) *Attorney, Agent, or Firm* — VIA LLP

(57) ABSTRACT

A mask frame, comprises a central conduit connection aperture and lateral arms having a 3-D curvature. The lateral arms extend: outwardly from a center of the frame, rearwardly, towards the patients ears, and upwardly, along a vector passing from below the nose to a point between the temple the top of the ear. The lateral arms "twist" along their length, such that a bottom margin of an end of each lateral arm is positioned further away from a notional vertical plane passing through the centre of the conduit connection aperture than a top margin.

Also provided is an anti-rotation feature which limits or prevents rotation between straps of a headgear, and the mask frame.

Further provided is a buckle for a closed loop headgear the buckle being formed with a plurality of openings and posts configured to form an angled headgear strap path through the buckle through which part of a headgear strap loop can pass. The buckle also comprises a friction loop opening through which a further of the headgear strap loop can pass, (Continued)

the angle of the angled path being such that the further part of the headgear strap loop frictionally engages the friction loop opening.

15 Claims, 33 Drawing Sheets

Related U.S. Application Data

(60) Provisional application No. 62/212,431, filed on Aug. 31, 2015, provisional application No. 62/077,071, filed on Nov. 7, 2014.

(51) Int. Cl.
*A44B 11/28* (2006.01)
*A61M 16/10* (2006.01)

(52) U.S. Cl.
CPC .... A61M 16/0825 (2014.02); A61M 16/0875 (2013.01); *A44B 11/28* (2013.01); *A61M 16/1095* (2014.02); *A61M 2202/0225* (2013.01); *A61M 2205/42* (2013.01)

(58) Field of Classification Search
CPC .......... A61M 16/0622; A61M 16/0633; A61M 16/065; A62B 18/084; A41D 13/11; A41D 13/1161; Y10T 24/3401
See application file for complete search history.

(56) References Cited

U.S. PATENT DOCUMENTS

| | | | |
|---|---|---|---|
| 7,370,652 | B2 | 5/2008 | Matula, Jr. et al. |
| 8,407,866 | B2 | 4/2013 | Pontaoe |
| 11,154,681 | B2 | 10/2021 | Huang et al. |
| 2004/0078943 | A1 | 4/2004 | Hede et al. |
| 2004/0221850 | A1* | 11/2004 | Ging ................ A61M 16/0622 128/207.11 |
| 2005/0028822 | A1 | 2/2005 | Sleeper et al. |
| 2005/0199242 | A1 | 9/2005 | Matula et al. |
| 2005/0205096 | A1 | 9/2005 | Matula, Jr. et al. |
| 2008/0190432 | A1 | 8/2008 | Blochlinger et al. |
| 2009/0032026 | A1 | 2/2009 | Price |
| 2009/0223521 | A1* | 9/2009 | Howard ............ A61M 16/0638 128/206.23 |
| 2009/0241961 | A1* | 10/2009 | McAuley ......... A61M 16/0816 128/207.18 |
| 2011/0232649 | A1 | 9/2011 | Collazo et al. |
| 2011/0240034 | A1* | 10/2011 | Ciccone ............ A61M 16/0493 128/207.17 |
| 2011/0247627 | A1 | 10/2011 | Omura et al. |
| 2011/0265796 | A1* | 11/2011 | Amarasinghe .... A61M 16/0683 128/206.28 |
| 2012/0132210 | A1 | 5/2012 | Matula, Jr. et al. |
| 2012/0227744 | A1 | 9/2012 | Radney |
| 2013/0008449 | A1 | 1/2013 | Busch et al. |
| 2013/0186404 | A1* | 7/2013 | Chien ............... A61M 16/0825 128/206.21 |
| 2014/0202463 | A1 | 7/2014 | Ging |
| 2015/0352308 | A1* | 12/2015 | Cullen ............. A61M 16/0683 128/205.25 |
| 2016/0121067 | A1* | 5/2016 | VanMiddendorp ........................ A61M 16/0875 128/207.17 |
| 2018/0078725 | A1* | 3/2018 | Richardson ....... A61M 16/0616 |

FOREIGN PATENT DOCUMENTS

| | | |
|---|---|---|
| CN | 1681552 | 10/2005 |
| CN | 101380497 A | 3/2009 |
| CN | 101951984 A | 1/2011 |
| CN | 202538197 | 11/2012 |
| TW | 201440826 | 11/2014 |
| WO | WO 2005/086943 | 9/2005 |
| WO | WO 2006/130903 | 12/2006 |
| WO | WO 2007/114492 | 10/2007 |
| WO | 2008011682 A1 | 1/2008 |
| WO | WO 2008/007985 | 1/2008 |
| WO | 2010073142 A1 | 7/2010 |
| WO | WO 2010/135785 | 12/2010 |
| WO | WO 2011/022751 | 3/2011 |
| WO | WO 2011/121466 | 10/2011 |
| WO | 2012040791 A1 | 4/2012 |
| WO | WO 2013/168041 | 11/2013 |
| WO | WO 2014/045136 | 3/2014 |
| WO | WO2014/110622 | 7/2014 |
| WO | 2014125066 A1 | 8/2014 |

\* cited by examiner

BREATHING APPARATUS WITH MASK ASSEMBLY FOR DELIVERING BREATHING GASES

INCORPORATION BY REFERENCE TO ANY PRIORITY APPLICATIONS

The present application is a continuation application of U.S. patent application Ser. No. 15/524,802, filed May 5, 2017, which is a 371 of International PCT/NZ2015/050186, Nov. 6, 2015, which claims priority benefit of U.S. Provisional Application Ser. No. 62/077,071, filed Nov. 7, 2014, and U.S. Provisional Application Ser. No. 62/212,431, filed Aug. 31, 2015, the disclosures of each of which are hereby incorporated by reference in their entireties.

BACKGROUND

Technical Field

The presently disclosed subject matter invention generally relates to interfaces for providing a supply of pressurised gas to a recipient.

Description of the Related Art

Breathing gases can be delivered to users with a variety of different mask styles and can be delivered for a variety of different purposes. For example, users can be ventilated using non-invasive ventilation (NIV). In addition, continuous positive airway pressure (CPAP) or variable airway pressure can be delivered using masks to treat a medical disorder, such as obstructive sleep apnea (OSA), chronic obstructive pulmonary disease (COPD), or congestive heart failure (CHF).

These non-invasive ventilation and pressure support therapies generally involve the placement of a user interface device, which is typically a nasal or nasal/oral mask, on the face of a user. The flow of breathing gas can be delivered from the pressure/flow generating device to the airway of the user through the mask.

Typically, patient interface devices include a mask frame that supports a sealing member. The sealing member contacts the facial surfaces of the user, including regions surrounding the nose, including the nose and the nares. Because such masks are typically worn for an extended period of time, a variety of concerns must be taken into consideration. For example, in providing CPAP to treat OSA, the user normally wears the mask all night long while he or she sleeps. One concern in such a situation is that the mask should be as comfortable as possible. It is also important that the mask provide a sufficient seal against a user's face without significant discomfort.

BRIEF SUMMARY

According to a first aspect of the invention there is provided a mask frame for a patient mask for delivering breathing gases to a patient, the mask frame comprising:
  a central region comprising a conduit connection aperture configured to be connected to a breathing gas delivery conduit, a notional central vertical plane extending through the centre of the conduit connection aperture; and
  first and second lateral arms each extending outwardly from the central region away from the central vertical plane;
  each lateral arm having a length and terminating in a distal end remote from the central region, each lateral arm comprising a top and bottom margin; wherein
  each lateral arm twists along its length such that the bottom margin at the end of each lateral arm is positioned further away from the notional central vertical plane than the top margin at the end of each lateral arm.

The lateral arms may extend:
laterally outwardly from the central region of the frame;
rearwardly, towards the patients ears; and
upwardly, so that the lateral arms are angled upwards such that they extend along a direction extending from the ends of the lateral arms to an area between the user's temples and ears. The lateral arms may extend upwardly along a vector passing from below the nose to a point between the temple at the top of the ear.

Each lateral arm may comprise a planar, generally oblong, strip or band, the end of each strip defining top and bottom corners at the top and bottom margins respectively, wherein the side arms twist along their length such that the bottom corner of the ends of the lateral arms are positioned further away from the central region of the frame than the top corners.

Each lateral arm may be tapered along its length, that is, the distance between the top and bottom margins reduces along at least part of the length of each lateral arm.

The ends of the lateral arms may be positioned below a notional horizontal mid plane that passes through the centre of the elbow connection aperture.

The end of each arm may comprise a headgear connector configured to connect the frame to headgear. The headgear connector may comprise a loop and a post configured to provide a connection point for a hook of a headgear clip attached to headgear.

In some embodiments, the headgear connector may comprise a rotation limiting formation configured to limit relative rotation between headgear connected to the headgear connector, and the mask frame. The rotation limiting formation may comprise an end stop against which the headgear abuts after a predetermined amount of relative rotation between the mask frame and headgear. The rotation limiting formation may be provided on the post. The rotation limiting formation may comprise two spaced apart end stops, relative movement between the headgear and the mask frame being limited by the distance between the two spaced apart end stops.

According to another aspect of the invention there is provided a mask assembly comprising the mask frame of the first aspect, and further comprising: headgear configured to be connected to the lateral arms of the mask frame; and a sealing cushion configured to be mounted on the mask frame.

According to a further aspect of the invention there is provided a mask assembly comprising a mask frame and a headgear configured to be connected to the mask frame, at least one of the mask frame and headgear comprising a connector comprising a post, the other of the mask frame and headgear comprising a connector comprising a hook configured to receive the post to connect the headgear to the mask frame such that the hook can rotate about the post towards and away from the mask frame, the mask assembly further comprising at least one rotation limiting formation configured to limit the extent of relative rotation between the hook and post.

The rotation limiting formation may comprise an end stop on one of the mask frame and headgear against which the other of the mask frame and headgear abuts after a predetermined amount of relative rotation between the mask frame and headgear. Two end stops may be provided, one on the mask frame, the other on the headgear, the end stops being configured to abut after a predetermined amount of relative rotation between the mask frame and headgear. One end stop may be provided on the hook, and the other end stop may be provided on the post.

At least one of the hook and post may comprise two spaced apart end stops, relative movement between the hook and post being limited by the distance between the two spaced apart end stops. One of the end stops may comprise a protrusion projecting from one of the hook and post, the other of the hook and post comprising a groove or recess having opposed ends, the opposed ends forming the two spaced part apart end stops, the protrusion being received in the groove or recess when the headgear is connected to the mask frame and being configured such that the protrusion moves within the groove or recess, between the opposed ends. The groove or recess may be provided on the post, the protrusion being provided on the hook.

According to another aspect of the invention there is provided a headgear connector assembly for connecting a headgear to a mask, the headgear connector assembly comprising a first connector comprising a post, and a second connector comprising a hook configured to receive the post to connect the first connector to the second connector such that the hook can rotate about the post, the headgear connector assembly further comprising at least one rotation limiting formation configured to limit the extent of relative rotation between the hook and post.

According to a further aspect of the invention there is provided a mask assembly comprising a mask frame and a headgear configured to be connected to the mask frame, the mask frame comprising:
  a central region comprising a conduit connection aperture configured to be connected to a breathing gas delivery conduit, a notional central vertical plane extending through the centre of the conduit connection aperture; and
  first and second lateral arms each extending outwardly from the central region;
  each lateral arm having a length and terminating in a distal end remote from the central region, each arm comprising a top and bottom margin; wherein
  each lateral arm twists along its length such that the bottom margin at the end of each lateral arm is positioned further away from the notional central vertical plane than the top margin at the end of each lateral arm;
  the headgear comprising straps having headgear connectors configured to be rotatably connected to the ends of the lateral arms;
  the mask assembly further comprising at least one rotation limiting formation configured to limit the extent of relative rotation between the mask frame and the headgear.

According to another aspect of the invention there is provided a buckle for a closed loop headgear, the buckle comprising:
  an inside face and an outside face extending between a bottom face and a top face;
  an inside post, a central post, and an outside post, each post extending between the top and bottom faces;
  a friction loop opening positioned between the inside post and the central post and configured to receive part of a headgear strap loop;
  a front opening formed at least on the inside face;
  an outside opening formed at least on the outside face;
  a headgear strap path extending between the front opening and the outside opening between the outside post and the central post, the path being configured to receive a return part of the headgear strap loop,
  wherein the front opening and the outside opening are offset such that the headgear strap path is angled.

The buckle may further comprise a strap attachment surface located on an inside surface of the outside post along the headgear strap path, the strap attachment surface being configured to be attached to a strap of the headgear.

The front opening may be formed adjacent the bottom face of the buckle, such that the front opening extends through both the bottom face and the inside face.

The outside opening may be formed a distance along the outside face so as to be spaced from the bottom face.

The friction loop opening may comprise top and bottom margins at least one of which is configured to frictionally engage the headgear strap loop by virtue of the angle of the return part of the headgear strap through the angled path.

According to a further aspect of the invention there is provided a closed loop headgear, comprising:
  a buckle according to the aspect of the invention above;
  a rear headgear section;
  at least one strap extending forward from the rear headgear section, wherein the at least one strap passes through the friction loop opening between the inside post and the central post.

The strap preferably continues, passing through a hook connector of the headgear and doubles back to form the return part of the headgear, passing back through the angled headgear strap path.

The strap may include a grip strap end that extends through the buckle from the outside opening. The grip strap end may have a length long enough to grasp between a thumb and one or two fingers. A dimple may be provided for additional grip at a distal end of the grip strap end.

The rear headgear section may comprise a bifurcated rear section.

According to a further aspect of the invention there is provided an elbow for connecting a breathing gas delivery conduit to a patient mask assembly, the elbow comprising:
  a ball joint section and a bottom portion;
  an elongate tube section connecting the ball joint section and the bottom portion; wherein
  the elongate tube section is narrower than the bottom portion and a largest diameter of the ball joint section.

The elongate tube section may include a front section configured to face away from the user, in use, and a rear section configured to face towards the user, in use, the front section being longer than the rear section.

The elongate tube section may form a truncated top where the front section and rear section connect to the ball joint section.

The elongate tube section may form an elbow having an angle $\Theta$ between a longitudinal axis of the elongate tube section, and a longitudinal axis of the ball joint section.

The front section of the elongate tube section may include a plurality of bias flow holes configured to enable $CO_2$ washout during use. The plurality of bias flow holes may be arranged in columns along a length of the front section, and in one embodiment the plurality of bias flow holes is arranged in two arrays of two columns with a space between the two arrays. The columns within each section may be offset, such that the bias flow holes of each row are nested with respect to each other, that is, the bias flow holes of one column are at least partially located in spaces between the bias flow holes of an adjacent column. One column may have a different number of bias flow holes from another column.

The elongate tube section may include side sections, each having a notch. The notches may be configured to receive a feature of a diffuser body having corresponding geometry.

In other aspects of the invention there is provided:

A: An apparatus as shown and described.

B: A mask frame, comprising: side arms having a 3-D curvature. The side arms may extend: outwardly from a center of the frame, rearwardly, towards the patients ears, and upwardly, along a vector passing from below the nose to a point between the temple the top of the ear. The side arms may twist along their length, such that bottom corner of the ends of the side arms are positioned further away from a central portion of the frame than the upper corners.

C: An elbow, comprising:
 a ball section and a wide bottom portion;
 an elongate tube section connecting the ball section and the wide bottom portion;
 the elongate tube section is narrower than the wide bottom end and a largest diameter of the ball section. The elongate tube section may include a long front section (facing away from the user and mask, in use) and a short rear section (facing towards the user and mask frame, in use). The elongate tube section may form a truncated top where the long front section and short rear section connect to the ball section. The elongate tube section generally forms an elbow having an angle Θ. The long front section of the elongated tube section may include a plurality of bias holes for CO2 washout during use. The plurality of bias holes may be arranged in columns along a length of the long front section. The plurality of bias holes may be arranged in two sections of two columns with a space between the two sections. The columns within each section may be offset, such that the bias holes of each row are nested with respect to each other. The elongated tube section may include side sections, each having a notch. The notches may be configured to receive a corresponding geometry of a diffuser body.

D: A buckle for a closed loop headgear, the buckle comprising:
 a bottom side and a top side;
 an inside post, a central post, and an outside post, each extending between the top and bottom sides;
 a friction loop opening between the inside post and the central post;
 a path comprising a front opening and an outside opening between the outside post and the central post, wherein the front opening and the outside are offset, forming an angled path. A strap attachment surface may be located on an inside of the outside post.

E: A closed loop headgear, may be provided comprising a buckle according to aspect D above and further comprising:
 at least one strap extending forward from a rear section passes through the buckle between the inside post and the central post. The strap may continue, passing through the hook connector and doubles back, passing back through the central post and outside post of the buckle. The strap may include a grip strap end that extends through the buckle from the outside opening. The grip strap end may have a length long enough to grasp between a thumb and one or two fingers. A dimple may be provided for additional grip at a distal end of the grip strap end. The rear section may be a bifurcated rear section.

Various features, aspects and advantages of the present invention can be implemented in any of a variety of manners. For example, while several embodiments will be described herein, sets or subsets of features from any of the embodiments can be used with sets or subsets of features from any of the other embodiments.

The term "comprising" is used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

These and other features, aspects and advantages of the present invention will be described with reference to the following drawings.

FIG. 1b is a side view of the flexible gas supply conduit, elbow assembly and swivel assembly of FIG. 1a.

FIG. 2b is a bottom, rear, and right side perspective view of the sealing cushion of FIG. 2a.

FIG. 3b is a bottom, rear, and right side perspective view of the mask frame of FIG. 3a.

DETAILED DESCRIPTION

As used herein the term "retaining forces" refers to any force applied by a headgear to retain a respiratory mask on a user's face.

Figure 1:
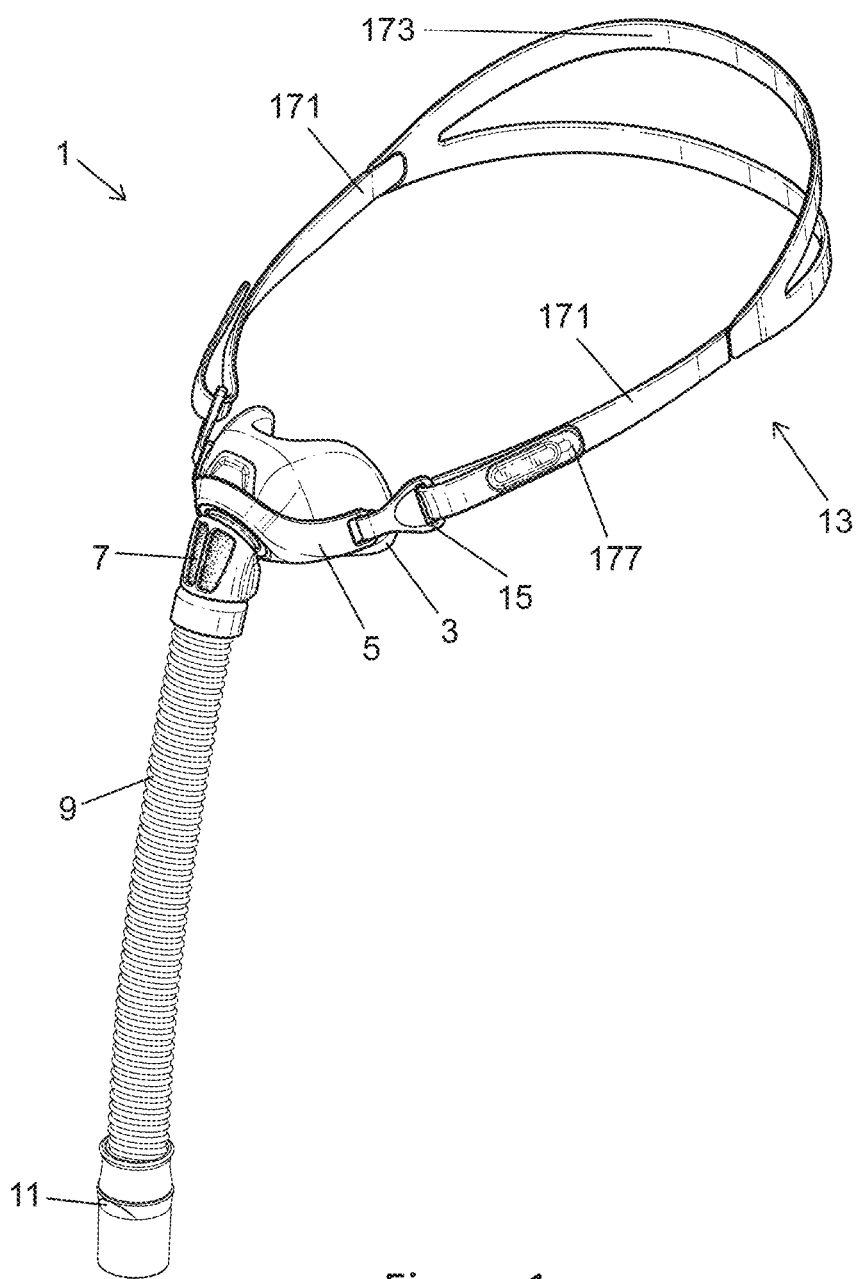
FIG. 1 is a top, front, and left side perspective view of a non-limiting exemplary embodiment of a nasal respiratory mask configured to provide a flow of pressurized breathing gases directly to a user's flares.

FIG. 1 shows a non-limiting exemplary embodiment of a nasal respiratory mask 1 configured to provide a flow of pressurized breathing gases directly to a user's nares. The respiratory mask 1 comprises a sealing cushion 3, mask frame 5, elbow assembly 7, flexible gas supply conduit 9, swivel assembly 11, headgear 13 and a pair of headgear clips 15.

Elbow and Flexible Gas Supply Conduit

Figure 1A:
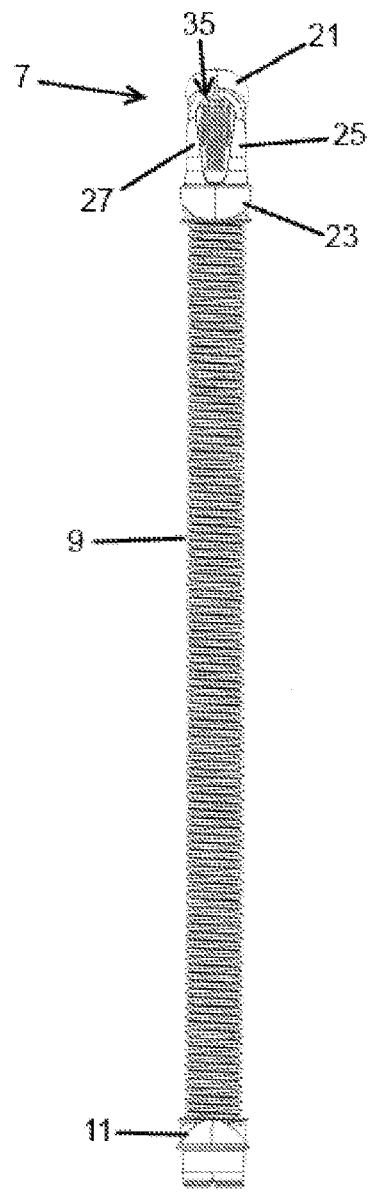
FIG. 1a is a front view of a flexible gas supply conduit, elbow assembly and swivel assembly that can be used with the mask of FIG. 1.
Figure 1B:
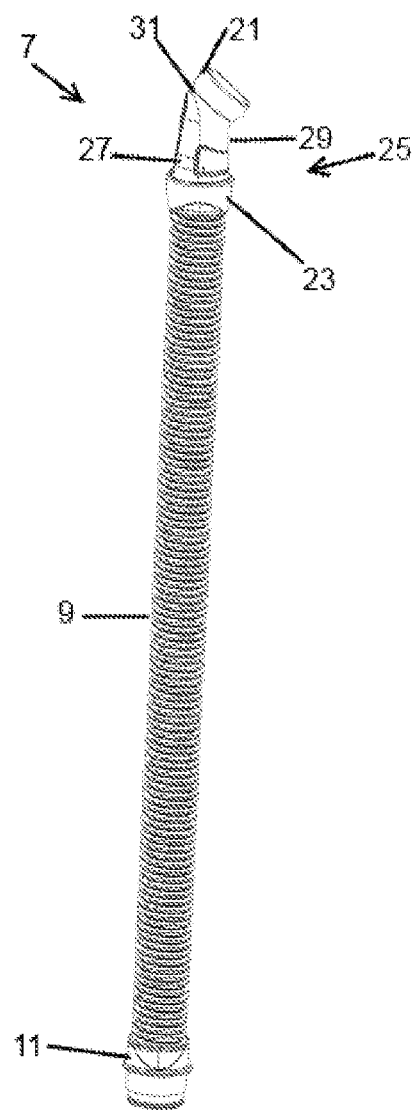
Figure 1C:
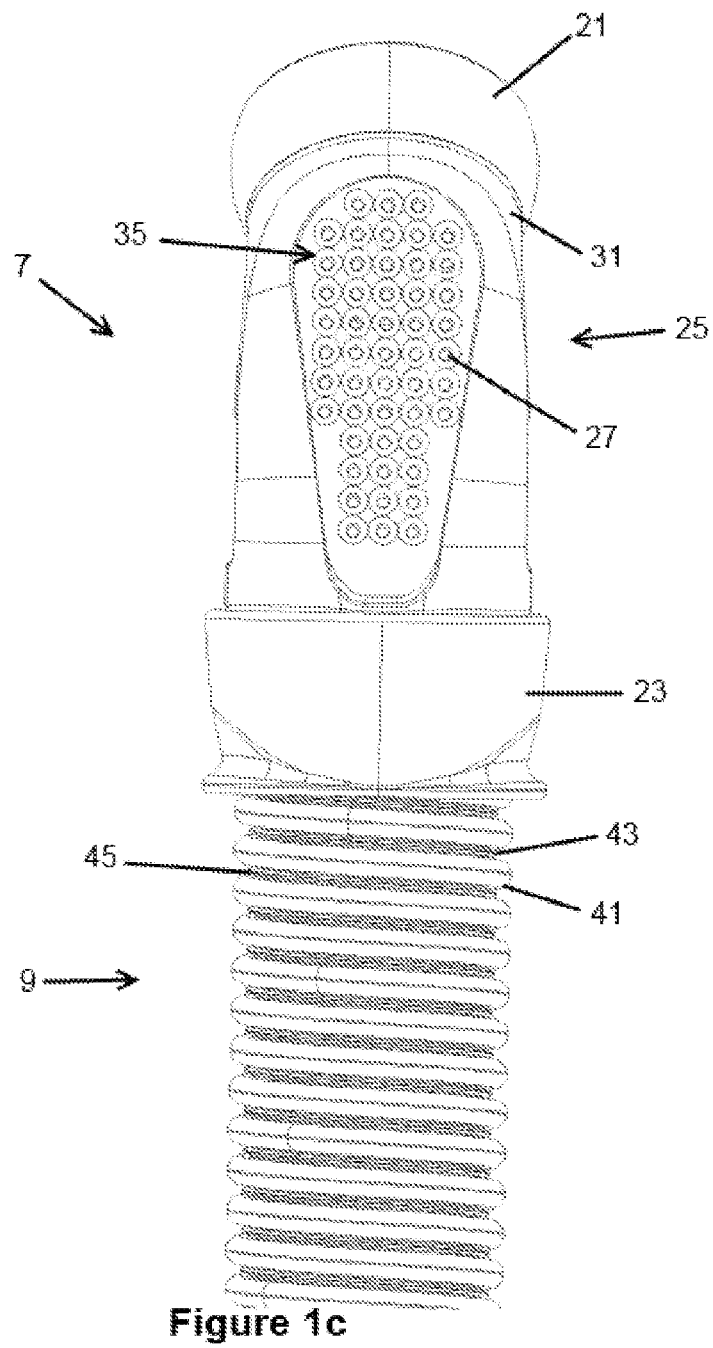
FIG. 1c is an enlarged perspective view of the elbow assembly and the flexible gas supply conduit of FIGS. 1a and 1b.
Figure 3A:
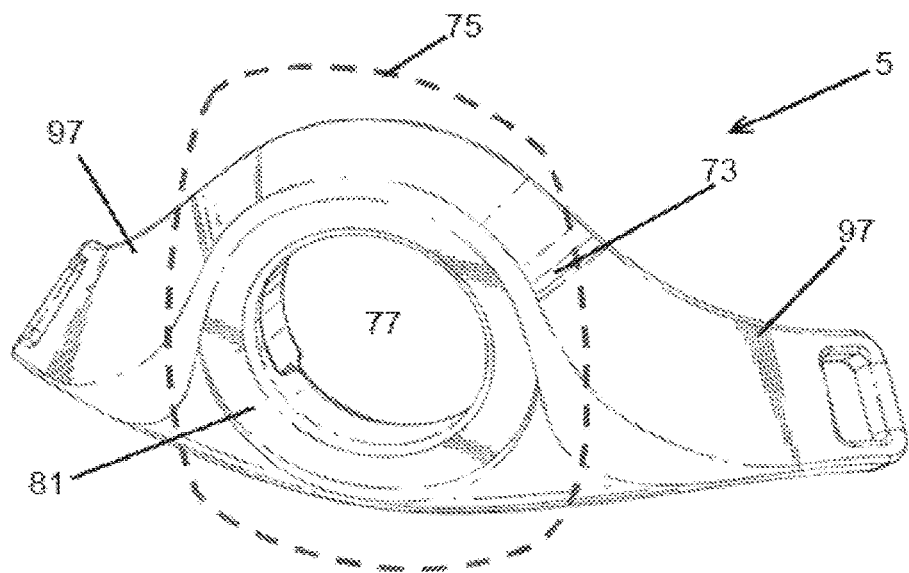
FIG. 3a is a top, front, and left side perspective view of a non-limiting exemplary embodiment of a mask frame comprising a proximal side, a distal side, a central region, and a lateral arm that extends from each side of the central region and which can be incorporated with the sealing cushion of FIGS. 2a and 2b into the mask of FIG. 1.

With reference to FIGS. 1a to 1c an elbow assembly is configured to connect to an elbow connection aperture 77 of the mask frame 5 (see e.g., FIGS. 1 and 3a). The elbow assembly 7 includes a ball joint section 21 and a wide bottom portion 23. An elongate tube section 25 connects the ball joint section 21 and the wide bottom portion 23. In this example, the elongate tube section 25 is narrower than the wide bottom portion 23 and a largest diameter of the ball joint section 21. The elongated tube section 25 includes a long front section 27 (facing away from the user and mask 1, in use) and a short rear section 29 (facing towards the user and mask frame 5, in use). The elongated tube section 25 forms a truncated top 31 where the long front section 27 and short rear section 29 connect to the ball joint section 21. In this configuration, the elongated tube section 25 generally forms an elbow having a bend along its length, such that a longitudinal axis of a conduit receiving section to the elbow assembly 7 is not aligned with a longitudinal axis of the ball joint section 21.

The long front section 27 of the elongated tube section 25 includes a plurality of bias flow holes 35 for CO2 washout during use. The plurality of bias flow holes 35 is arranged in columns along a length of the long front section, the columns generally being aligned with the longitudinal axis of the elongated tube section 25. In particular, in this example, the plurality of bias flow holes 35 is arranged in three central longer columns and two lateral shorter columns with a space between the two sections. Each long central column has twelve bias flow holes in this example, and each short lateral column has seven bias flow holes. The columns are arranged on a tapering, keyhole shaped region of the long front section 27.

The wide bottom portion 23 is a short tube section that is concentrically offset from a conduit receiving section, such that an annular channel is formed between the two. The conduit receiving section is configured to receive the flexible gas supply conduit 9 on its outer surfaces. The annular channel is configured to receive and retain the end of the flexible gas supply conduit 9. The conduit receiving section includes an external thread, which is configured to retain the flexible gas supply conduit 9. The wide bottom portion 23 is configured to hide the end of the flexible gas supply conduit 9.

The flexible gas supply conduit 9 is a flexible tube comprising an external helical bead 41 and a thin conduit wall 43, supported by the bead 41. The bead 41 may contain an electrically conducting wire or strip for providing heating to the conduit 9, or for transferring data or sensor signals along the conduit 9. The thin wall 43 comprises a radially outwardly directed fold or bend 45 between each adjacent helical coil. This outwardly directed fold 45 does not project outwardly as far as the bead 41, such that the fold diameter is less than the bead diameter, when the conduit 9 is in a neutral condition, as shown in FIGS. 1a to 1c. The bead 41, and fold 45, are configured such that the conduit 9 is flexible such that it can bend and can extend or contract longitudinally. The fold 45 allows the conduit 9 to bend such that the conduit 9 is not straight in use. The fold 45 also allows the length of the conduit 9 to be varied. The bead 41 may be configured as a spring such that any flexing, extending or contracting of the conduit 9 is elastic, with the bead 41 and/or the fold, returning the conduit 9 to its neutral condition, in the absence of force applied the to the ends of the conduit 9.

Sealing Cushion

The sealing cushion 3 is configured to engage with and form a substantially airtight seal with the nares and outwardly facing surfaces of a user's nose, such that pressurized breathable gases are delivered directly to the nasal passage. Such a seal is described in PCT/NZ2014/000150 (publication number WO2015009172), filed 17 Jul. 2014, the entire contents of which are hereby incorporated by reference.

The sealing cushion 3 preferably comprises a seal body 51 and a mask frame connector 53. The seal body 51 can be formed of a soft and flexible material such that a supple pocket or envelope, that defines an inner cavity, is provided. The seal body 51 can be made of any appropriate material such as, but not limited to latex, vinyl, silicone or polyurethane.

Figure 2A:
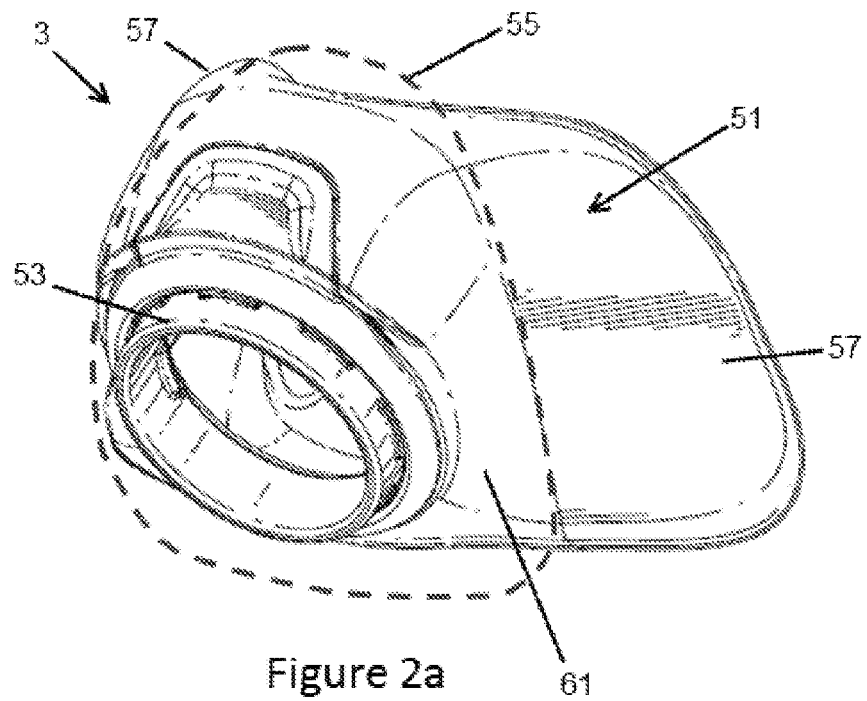
FIG. 2a is a top, front, and left side perspective view of a non-limiting exemplary embodiment of a sealing cushion that can be incorporated into the mask of FIG. 1.
Figure 2B:
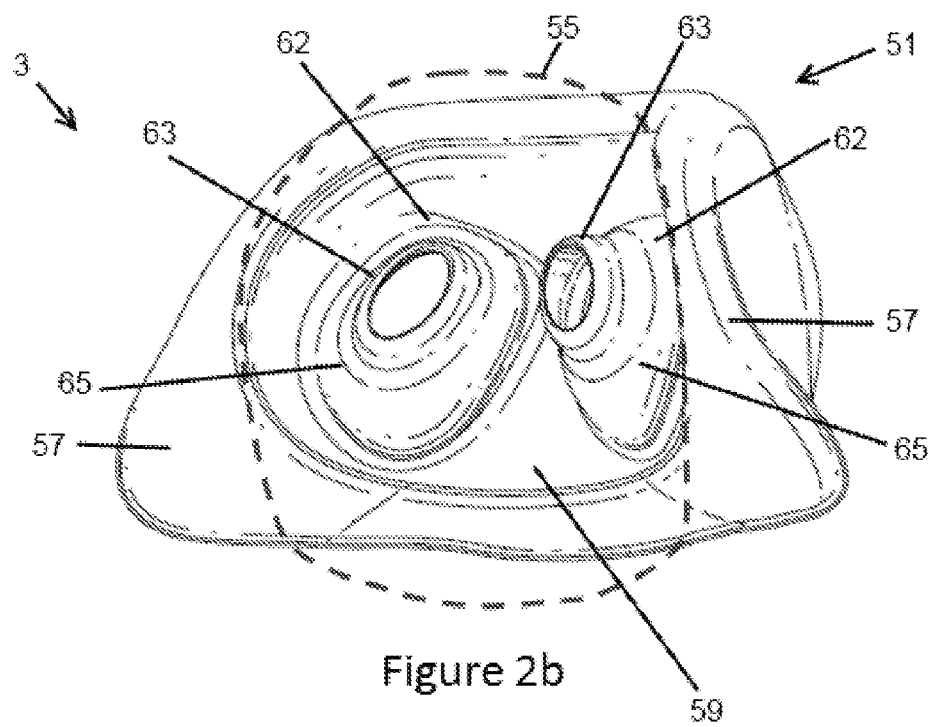

Referring to FIGS. 2a and 2b the seal body 51 comprises a central portion 55 and first and second lateral portions 57 extending from each side of the central portion 55. The seal body 51 further comprises an internal side 59 (FIG. 2b) and an external side 61 (FIG. 2a). The internal side 59 is positioned proximal to the user's face in use and is configured to provide sealing, stabilizing and locating surfaces. The external side 61 is positioned distal to the user's face, relative to the internal side 59, in use, and is configured to provide structure to the sealing cushion 3.

The internal side 59 of the central portion 55 is configured to extend across a base of a user's nose and the internal side of each of the lateral portions 57 is configured to curve around and extend across a lateral side of the nose. These lateral portions 57 can form a perimeter seal on outwardly facing surfaces or flanks of the nose. The lateral portions 57 are outwardly flared away from the user's nose at the lower corners, such that they contact the user's cheeks without digging in. The contact between the lateral portions 57 and the user's cheeks provides a location through which retaining forces can be applied by the headgear 13 to the user's face, in order to stabilize the respiratory mask 1.

The internal side 59 has a thin wall thickness such that the seal body 51 is supple and capable of conforming to the geometry of the user's nose. The external side 61 comprises a greater wall thickness than the internal side 59, such that it provides structure and stability to the more supple internal side 59.

The internal side 59 of the central portion 55 further comprises a pair of prongs 62. The prongs 62 comprise air delivery openings 63 and locating surfaces 65. The air delivery openings 63 are configured to allow a flow of pressurized breathable gases to pass from within the seal body 51 to the user's airways. The locating surfaces 65 are configured to provide means of locating and sealing the prongs 62 within the user's nares and positioning the sealing cushion 3 on the nose.

The mask frame connector 53 is located within the external side 61 of the central portion 55, and comprises a substantially rigid ring that is permanently attached to the seal body 51, by any appropriate means. The mask frame connector 53 is configured to provide an inlet through which pressurized breathable air is delivered into the seal body 51. The mask frame connector 53 is further configured to provide a substantially airtight connection between the sealing cushion 3 and the mask frame 5; wherein the mask frame 5 and the sealing cushion 3 can be repeatedly assembled and disassembled. The connection between the mask frame 5 and the mask frame connector 53 may be achieved by any appropriate means including but not limited to snap-fit, friction fit, threaded or bayonet mechanisms.

Mask Frame

Figure 3B:
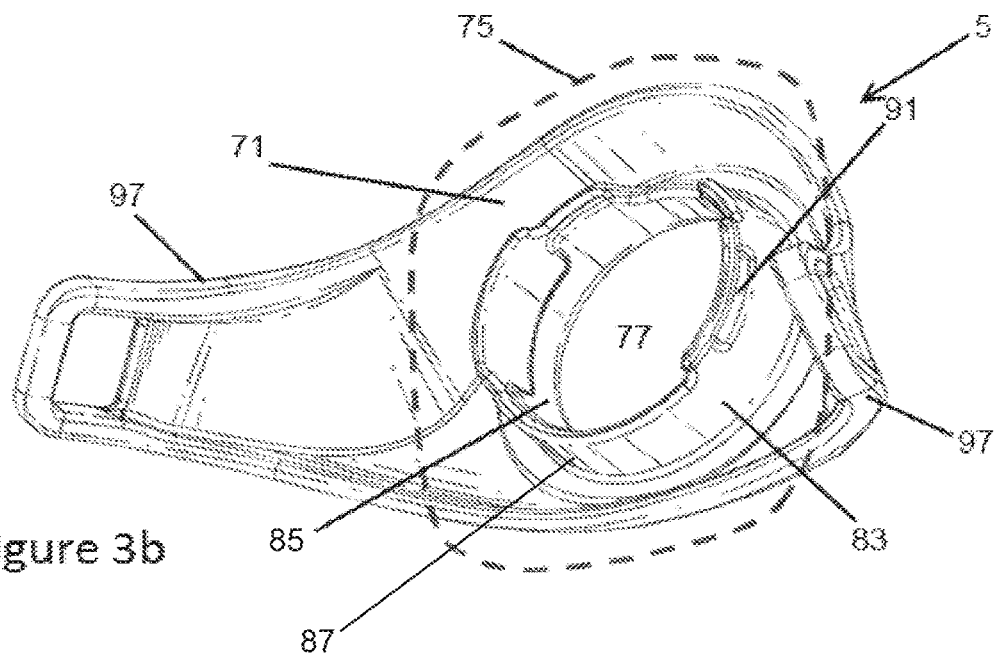

As shown in FIGS. 3a and 3b the mask frame 5 comprises a proximal side 71 (FIG. 3b), a distal side 73 (FIG. 3a), a central region 75, and first and second lateral arms 97 that extend from each side of the central region 75. The lateral arms 97 each comprise generally oblong planar strips or bands having elongate top and bottom margins extending along the length of each arm 97. The lateral arms 97 are thus relatively wide when viewed from the front, but relatively narrow when viewed from above. The proximal side 71 is configured to be adjacent to the sealing cushion 3 and proximal to the user's face in use. The distal side 73 forms the external surface of the mask frame 5. The distal side 73 of the central region 75 comprises an elbow connection aperture 77 which can optionally be circular. The elbow connection aperture 77 is configured to receive the ball joint 21 of the elbow assembly 17. A planar surface 81 extends radially outwardly from the elbow connection aperture 77.

The proximal side 71 of the central region 75 comprises an annular wall 83 that projects in a rearward direction towards the sealing cushion 3, around the perimeter of the elbow connection aperture 77.

The annular wall 83 comprises an internal surface 85 and an external surface 87. The internal surface 85 comprises a concave spherical section, configured to form a ball joint socket. The ball joint socket is configured to connect to corresponding geometry on the elbow assembly 17, namely the ball joint section 21. The external surface 87 comprises one or more indentations 91 configured to be coupled to corresponding geometry on the mask frame connector 53 of the sealing cushion 3, such that a connection between the mask frame 5 and the cushioning seal is achieved.

Figure 4:
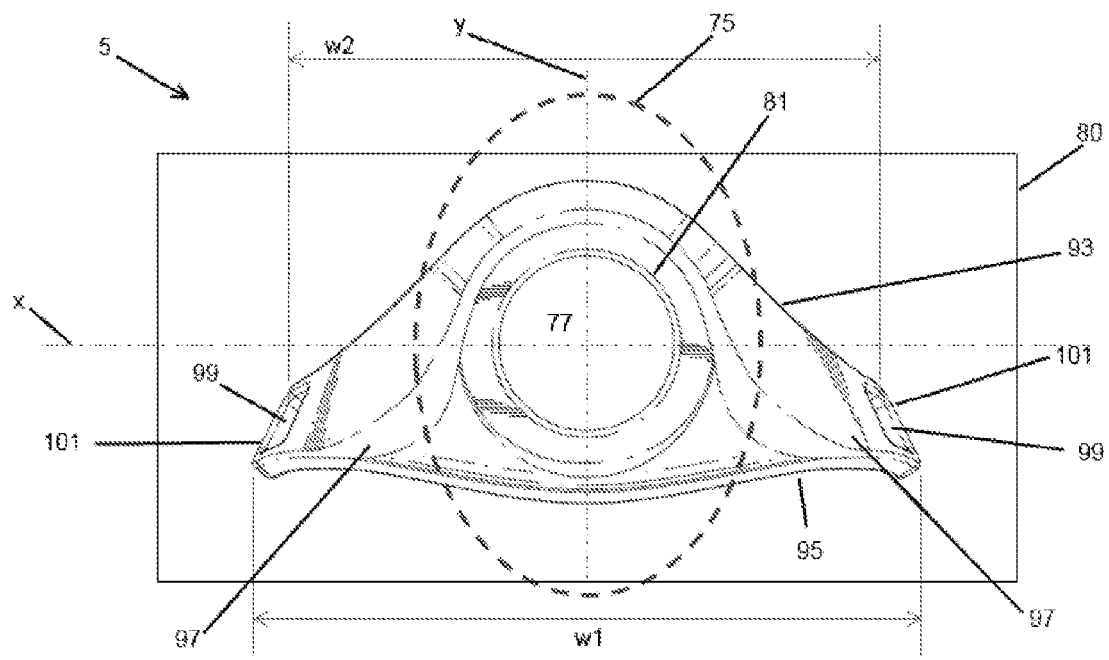
FIG. 4 shows an orthogonal front view of the mask frame of FIGS. 3a-3b.

FIG. 4 shows an orthogonal front view of the mask frame 5. The view is perpendicular to a front plane 80 that is coincident with the planar surface 81 (see e.g., FIG. 3a). The mask frame 5 is symmetrical about a central vertical plane 'y', which passed through a center of the elbow connection aperture 77. The mask frame 5 further comprises a top edge margin 93 and a bottom edge margin 95, both of which extend from one lateral arm 97 through the central region 75 to the other lateral arm 97. The top edge margin 93 is positioned such that it is above the bottom edge margin 95 both in the view of FIG. 4 and in use. Within the central region 75, the top edge margin 93 is offset from and substantially follows the curvature of the elbow connection aperture 77. The top edge margin 93 tapers outwardly (horizontally away from the central vertical plane 'y') in a largely downward direction as it transitions from the central region 75 to each of the lateral arms 97. The bottom edge margin 95 curves outwardly in a somewhat upward direction from the central vertical plane 'y' region. As it transitions from the ends of the central region 75 towards the end of each of the lateral arms 97 it curves in a slightly downward direction.

The tapered transitions of the top edge margin 93 and the bottom edge margin 95 form the lateral arms 97, which are substantially elongate tapered members extending outwardly from each side of the central region 75. The lateral arms 97 comprise a loop 99 and a post 101 configured to provide a connection point for the headgear clips (see e.g., FIG. 14A). The loop 99 is a rectangular aperture that extends through the lateral arms 97 perpendicular to the distal side. In alternative embodiments the aperture may have any appropriate shape. The post 101 is formed by the outer wall of the loop 99 and forms the outer ends of the lateral arms 97, and is substantially cylindrical. The post 101 is angled in an upwards direction towards the central region 77. This is shown by the width $w_1$ of the bottom edge being wider than the width $w_2$ of the top edge.

The ends of the lateral arms 97 are positioned substantially below a horizontal mid plane 'x' that is perpendicular to the front plane and vertical plane y and passes through the center of the elbow connection aperture 77. Thus, the lateral arms 97 taper towards the bottom half of the mask frame 5.

Figure 5:
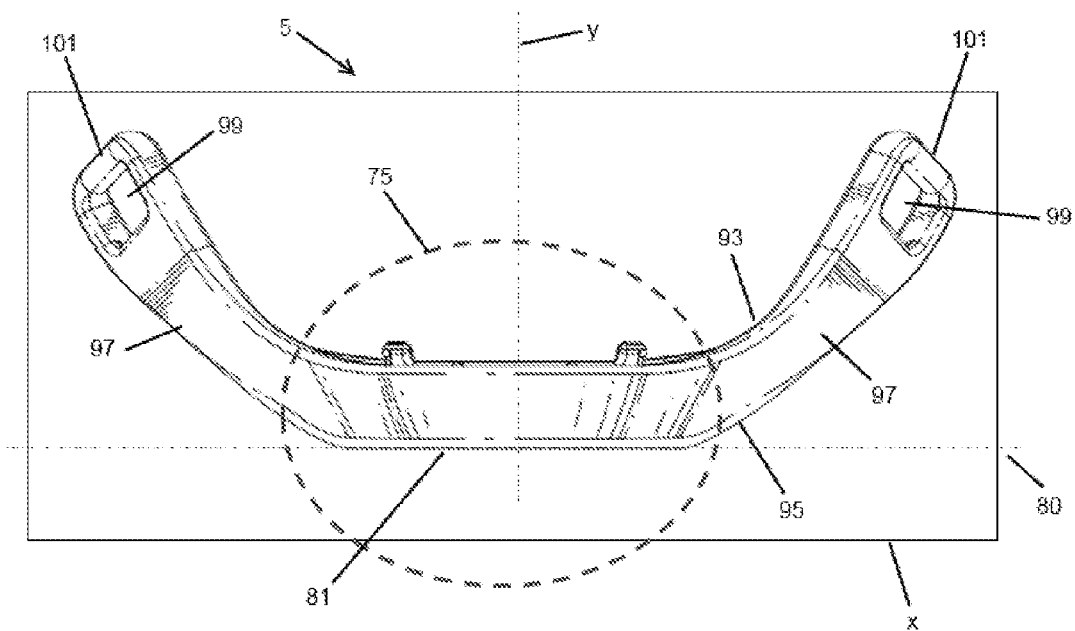
FIG. 5 shows a corresponding orthogonal top view of the mask frame of FIGS. 3a-3b.

FIG. 5 shows a corresponding orthogonal top view of the mask frame 5. It shows that the lateral arms 97 also extend in a rearward direction (distal to proximal) from the planar surface 81.

Figure 6:
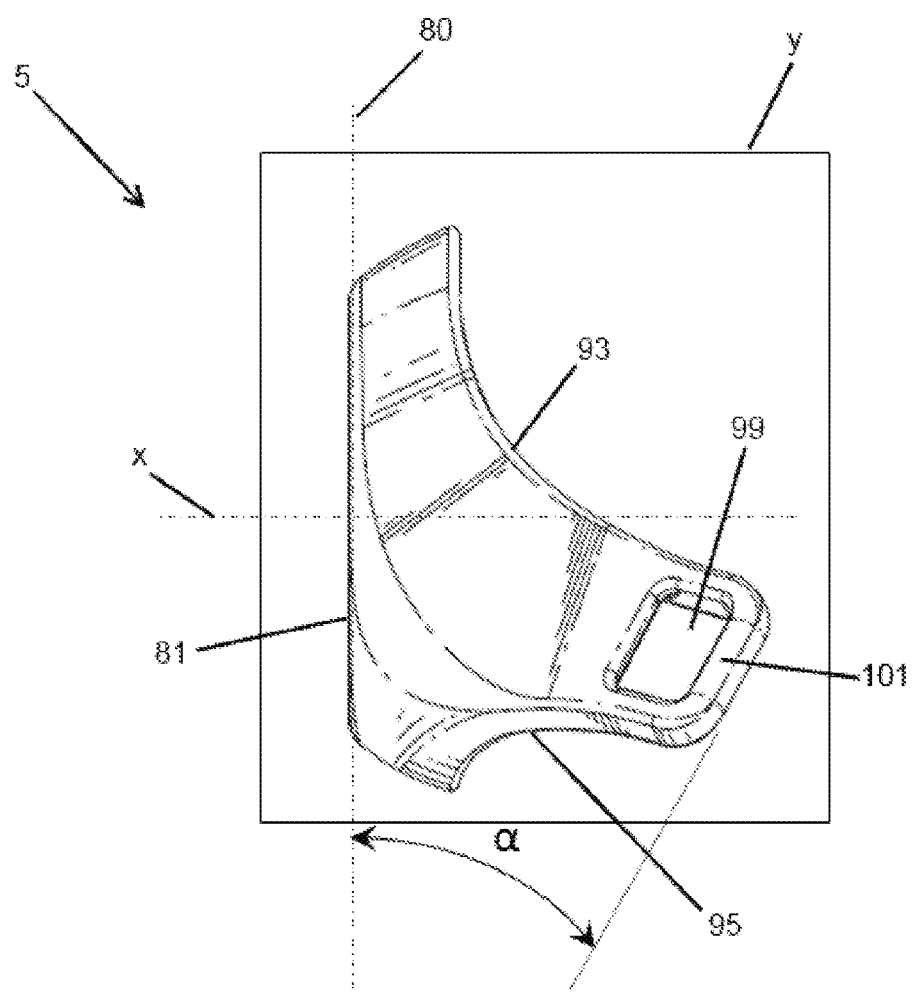
FIG. 6 shows a corresponding orthogonal side view of the mask frame of FIGS. 3a-3b.

FIG. 6 shows a corresponding orthogonal side view of the mask frame 5. It can be seen that the end of the bottom edge margin 95 is closer to the front plane than the end of the top edge margin 93. This results in the length of the post 101 forming an acute angle α with the front plane.

Figure 7:
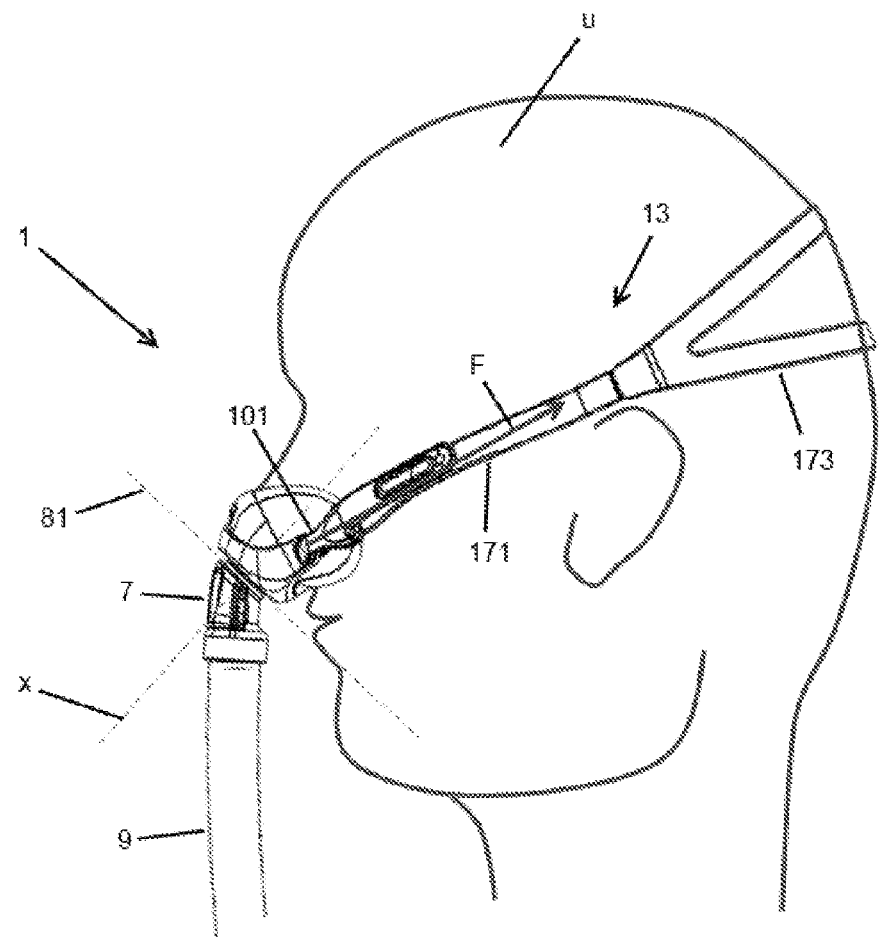
FIG. 7 is a side view of a respiratory mask in use on a user U.
Figure 8:
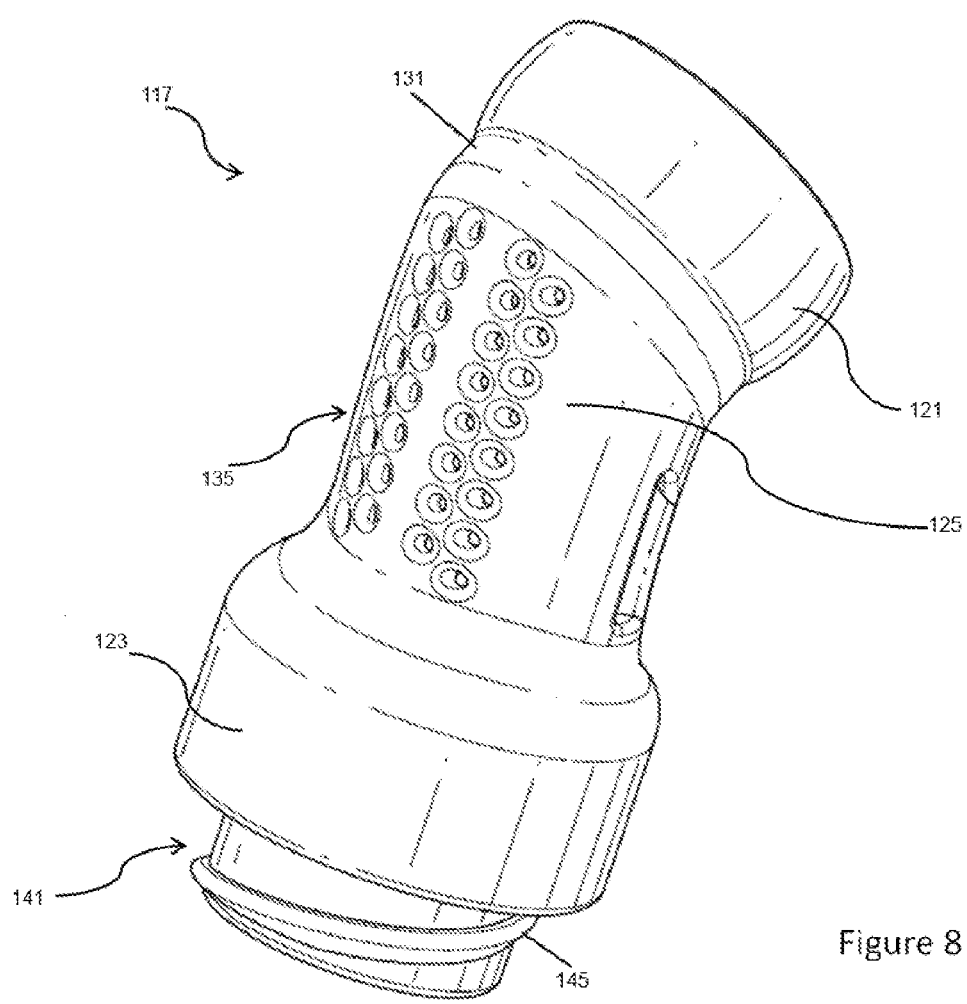
FIGS. 8 and 8A-8F show a non-limiting exemplary embodiment of an elbow that can be incorporated into the mask of FIG. 1, optionally with the sealing cushion of FIGS. 2a-2b and the mask frame of FIGS. 3a-3b.
Figure 8A:
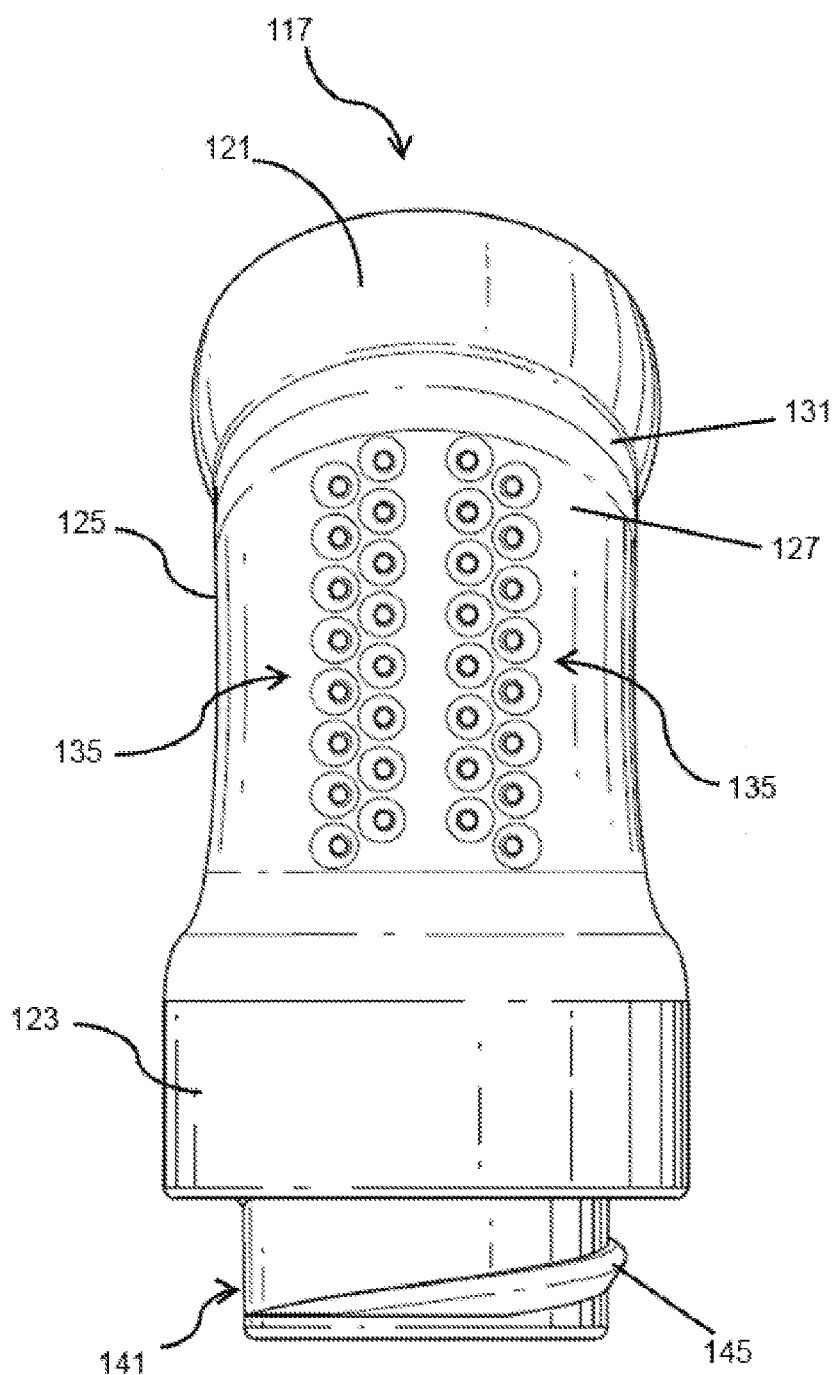
Figure 8B:
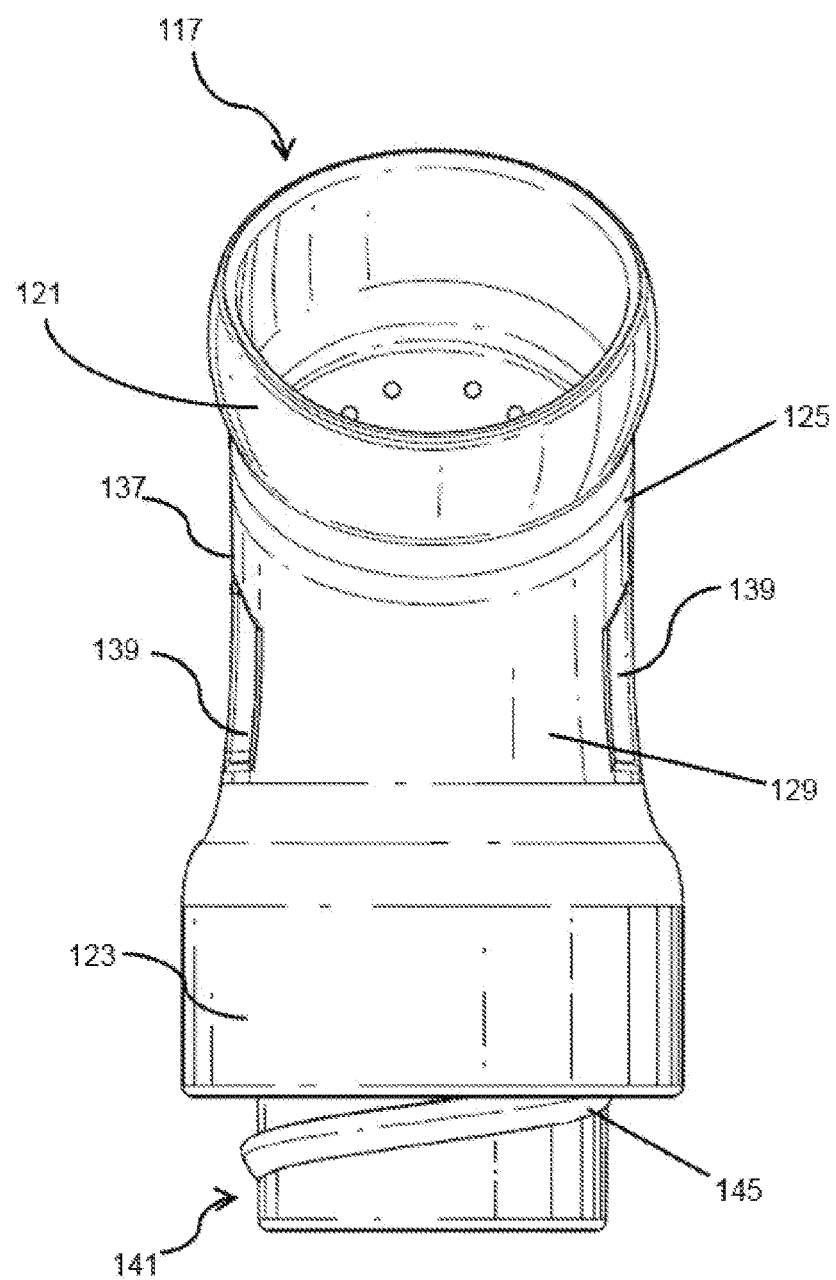
Figure 8C:
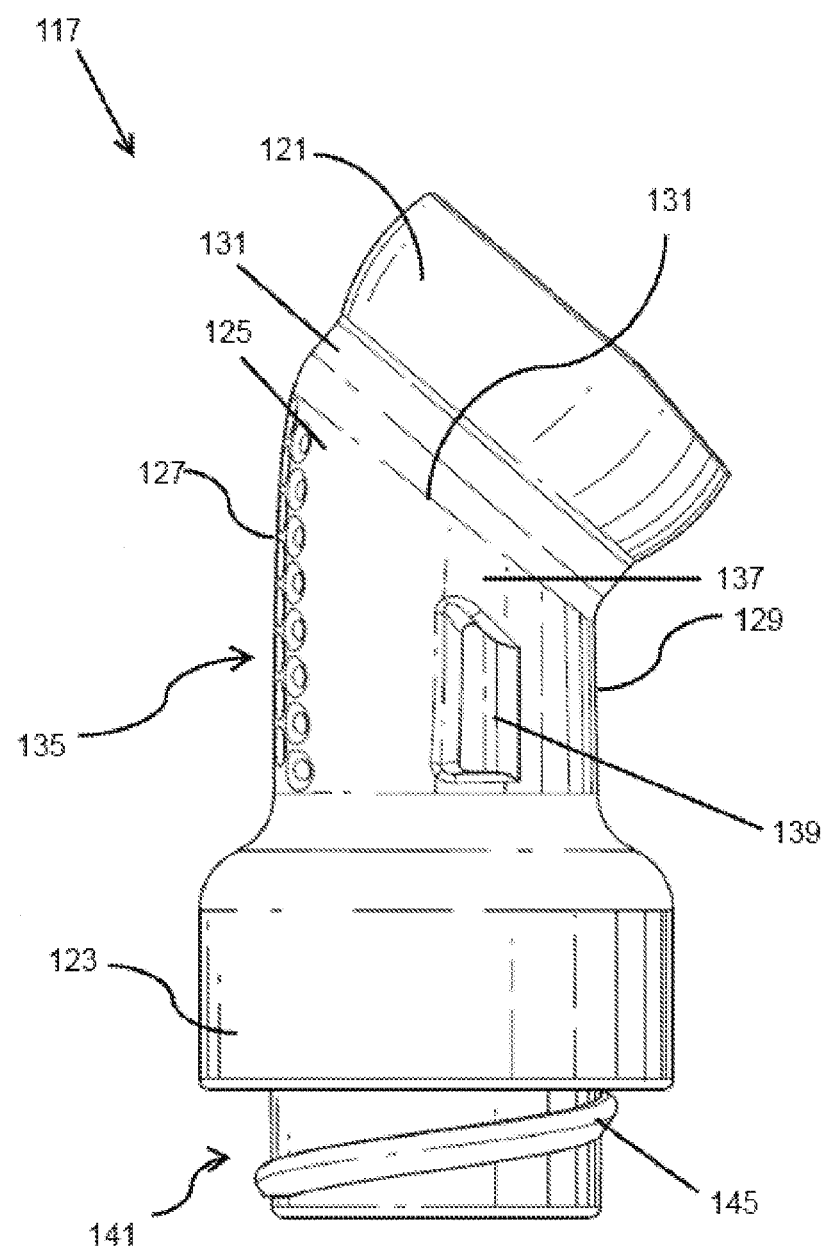
Figure 8D:
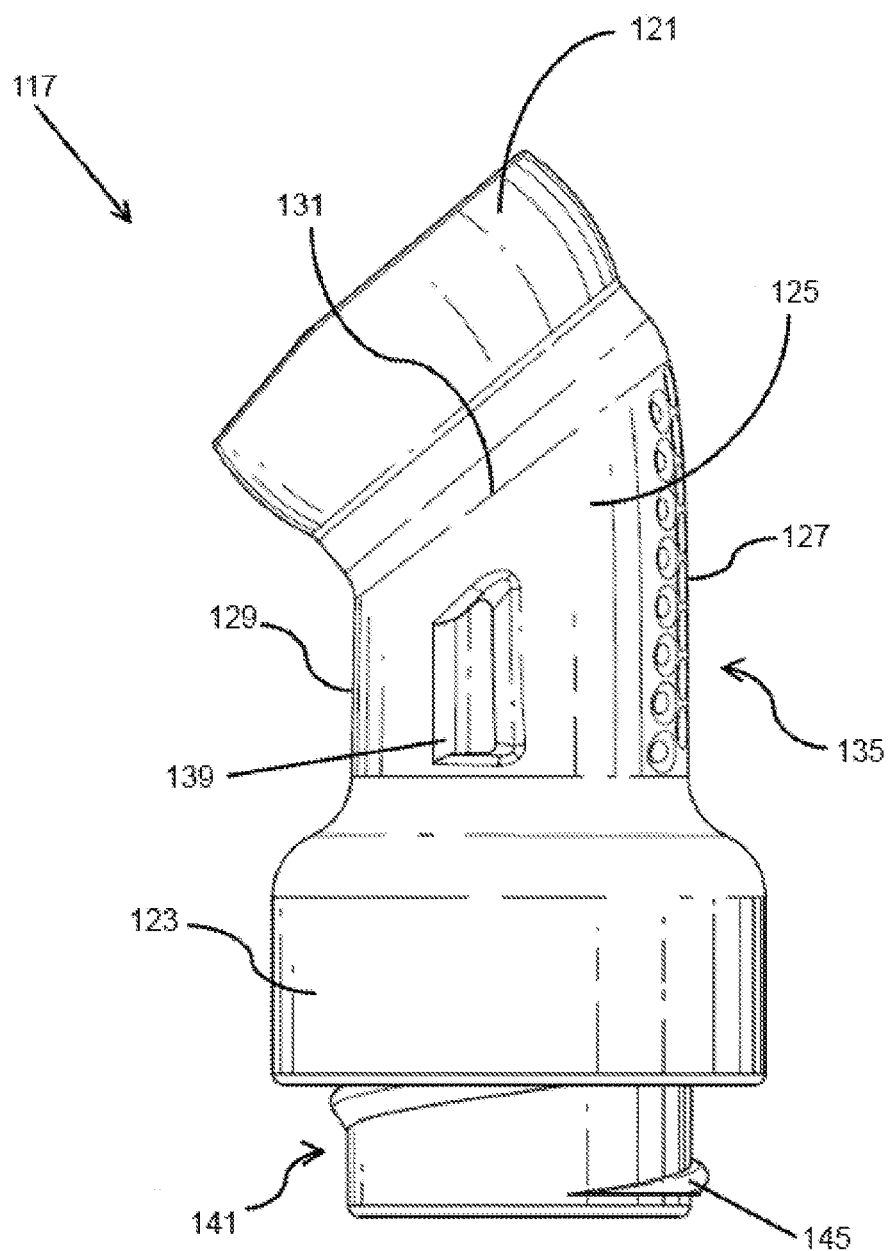
Figure 8E:
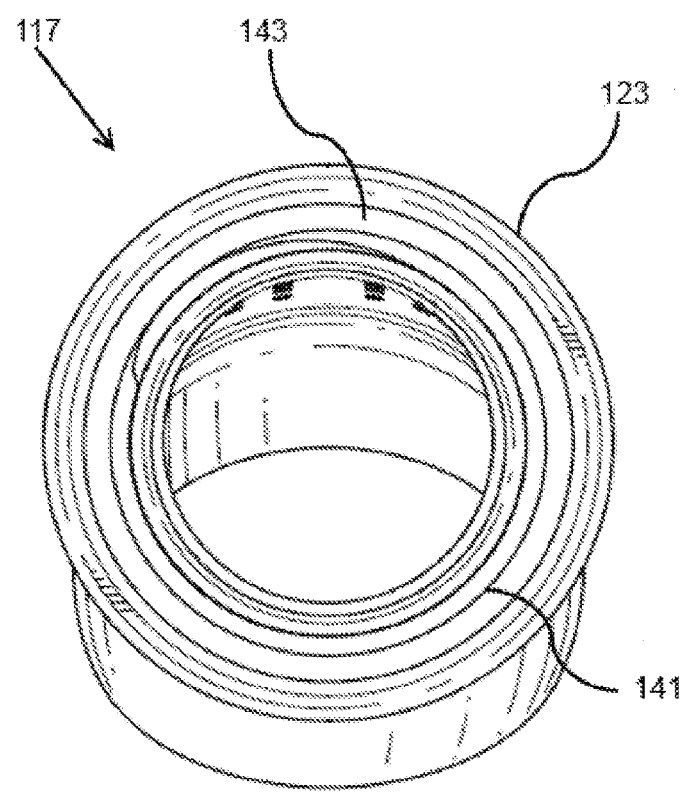
Figure 8F:
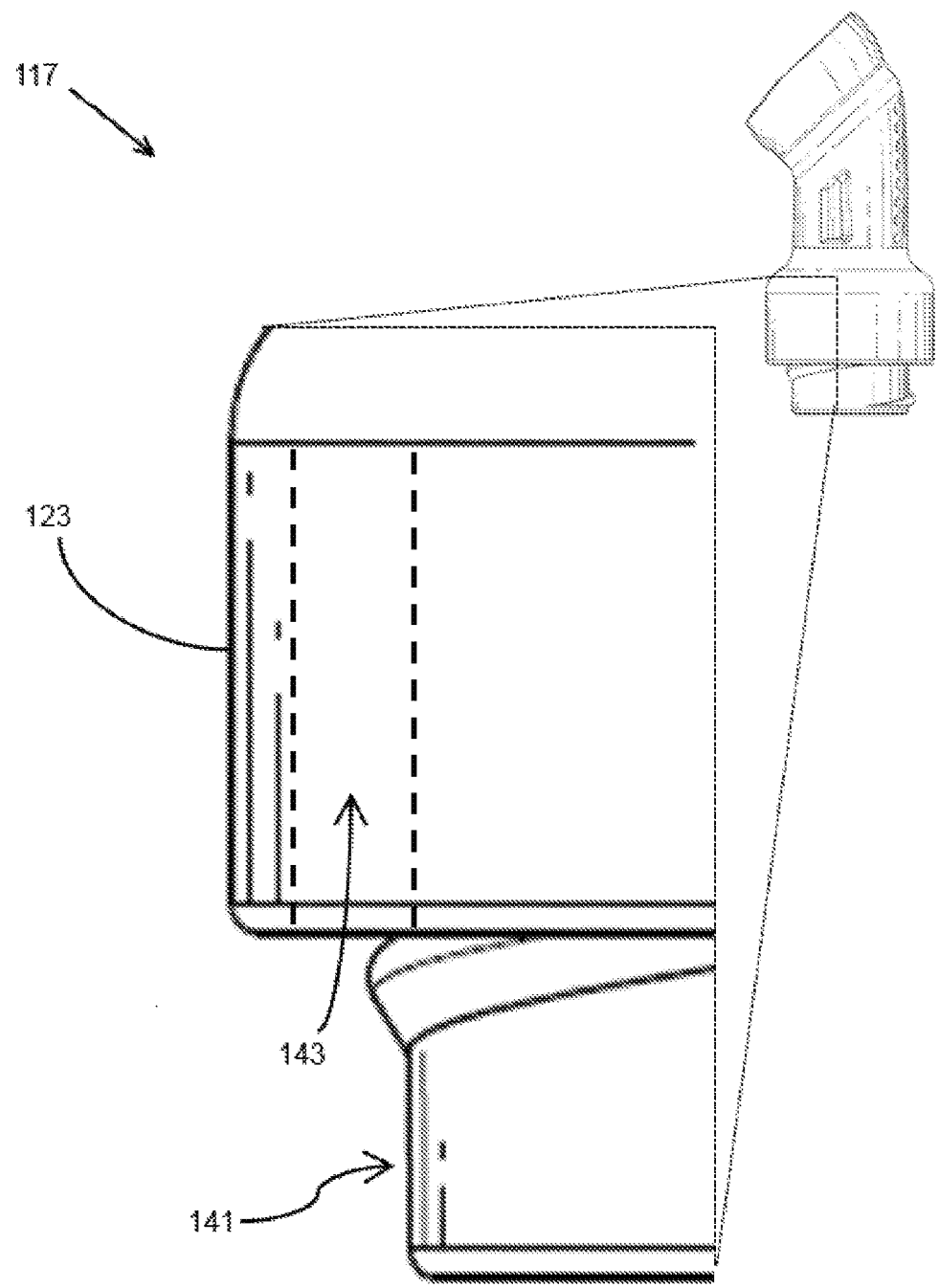
Figure 9A:
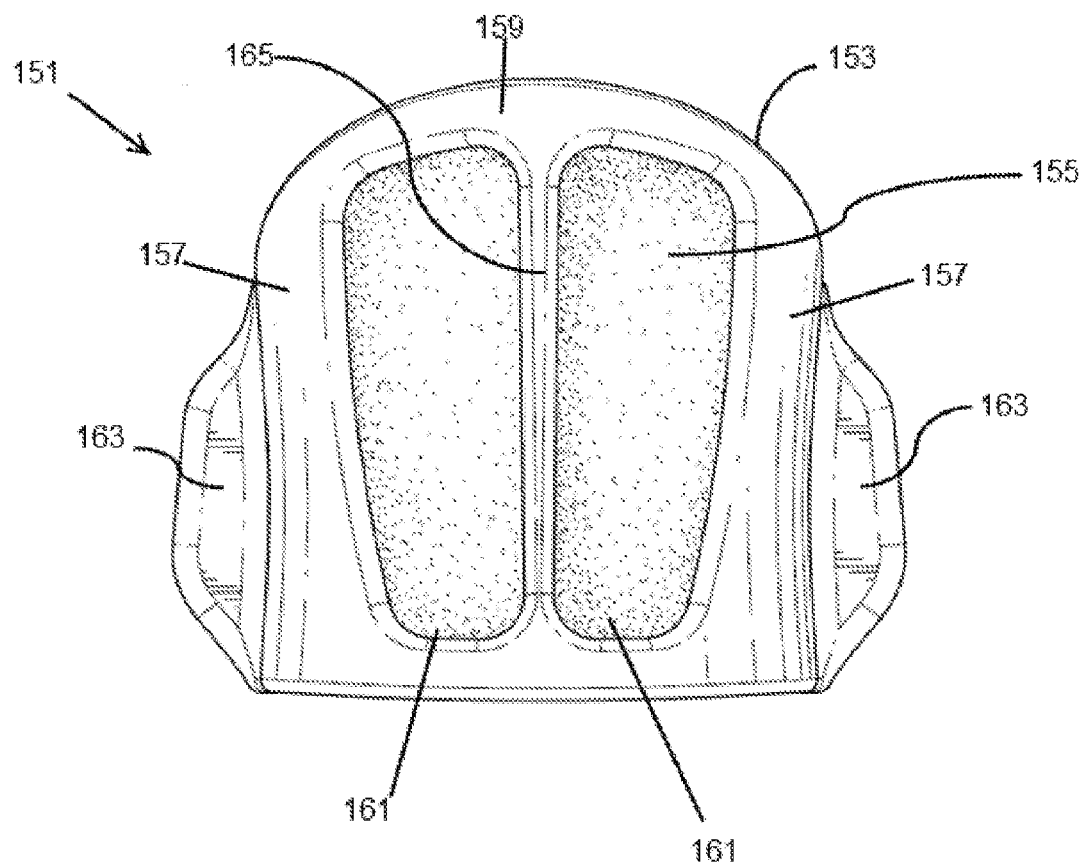
FIGS. 9A-D show a non-limiting exemplary embodiment of a diffuser configured to connect to the elbow of FIGS. 8 and 8A-8F.
Figure 9B:
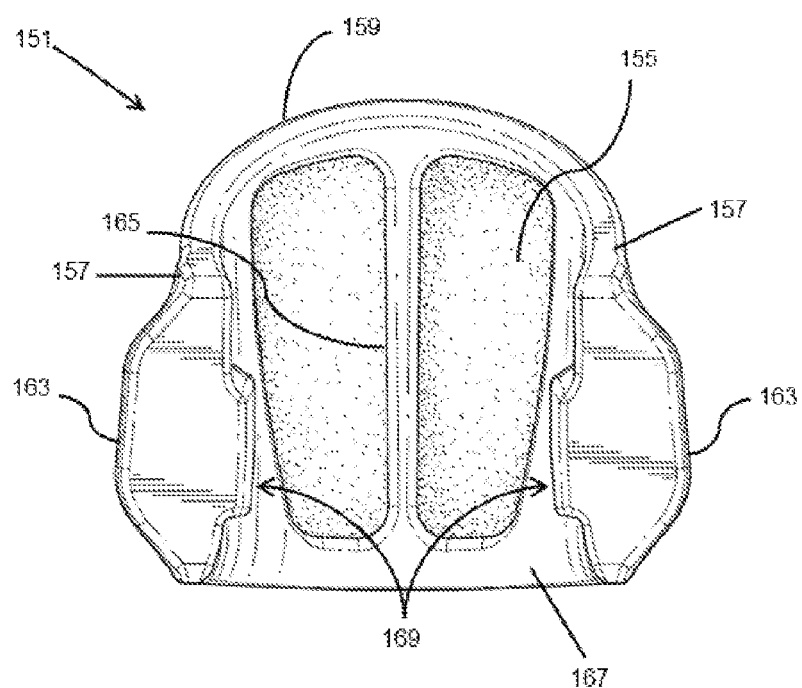
Figure 9C:
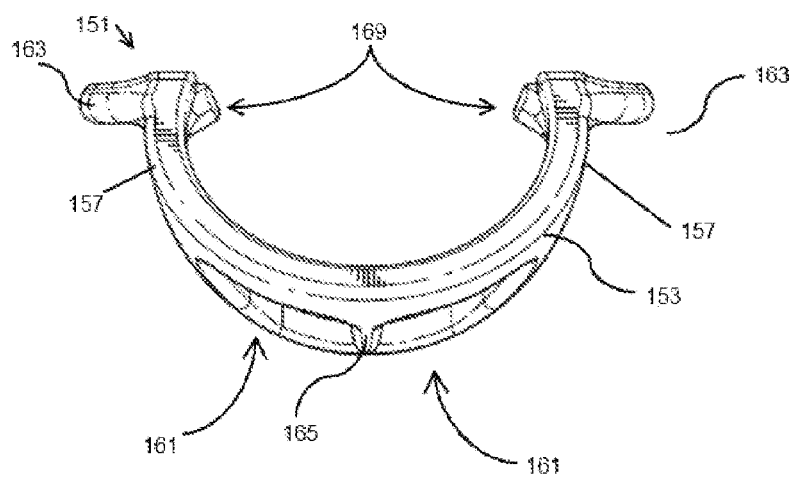
Figure 9D:
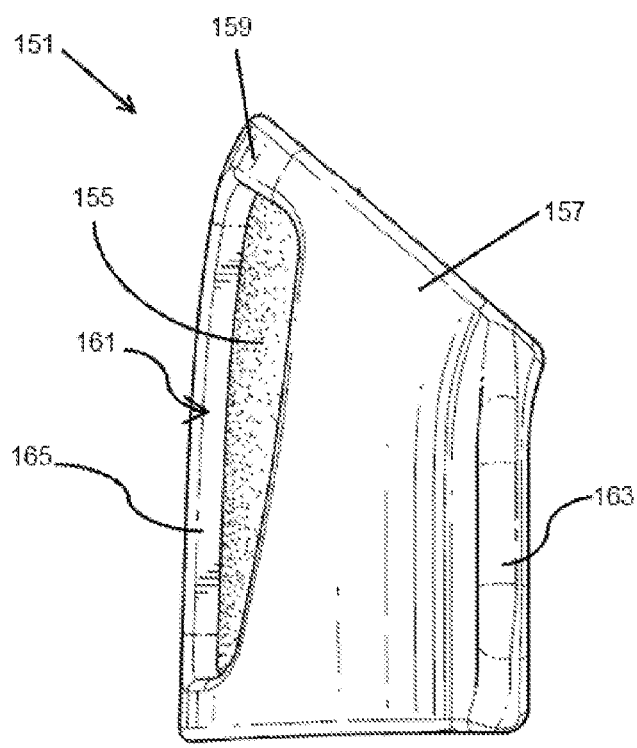
Figure 10A:
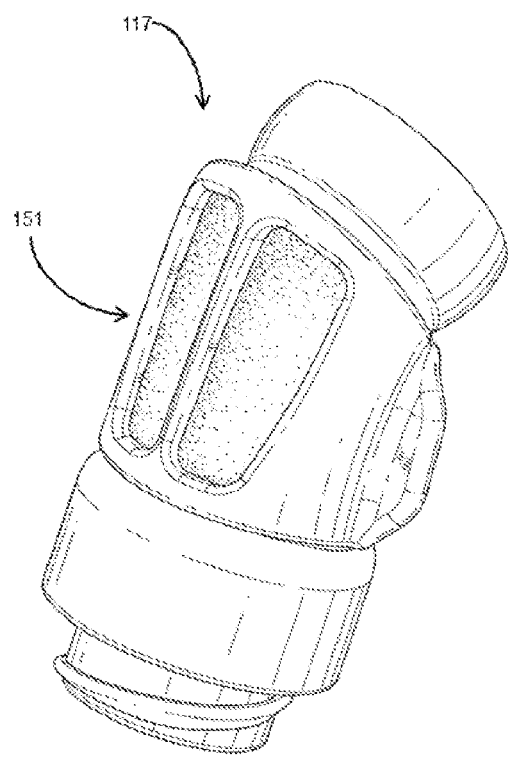
FIGS. 10A-10E show the elbow of FIGS. 8 and 8A-8F and diffuser assembly, wherein the diffuser is connected to the elbow such that the bias holes are covered.
Figure 10B:
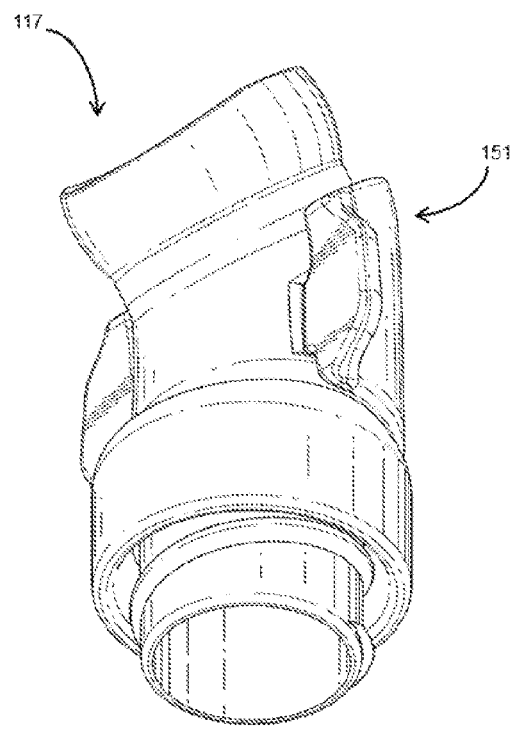
Figure 10C:
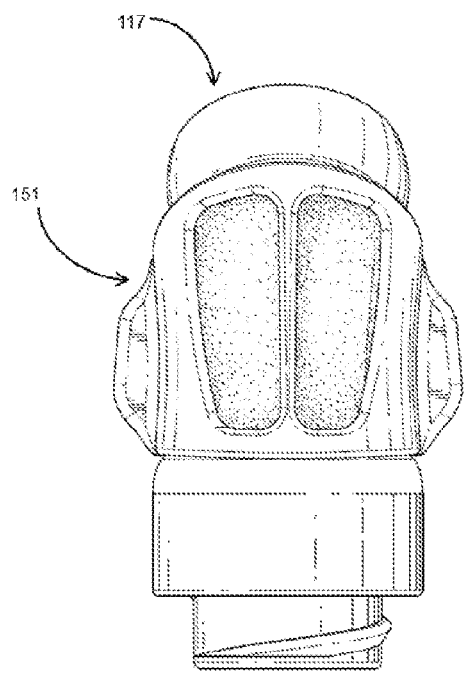
Figure 10D:
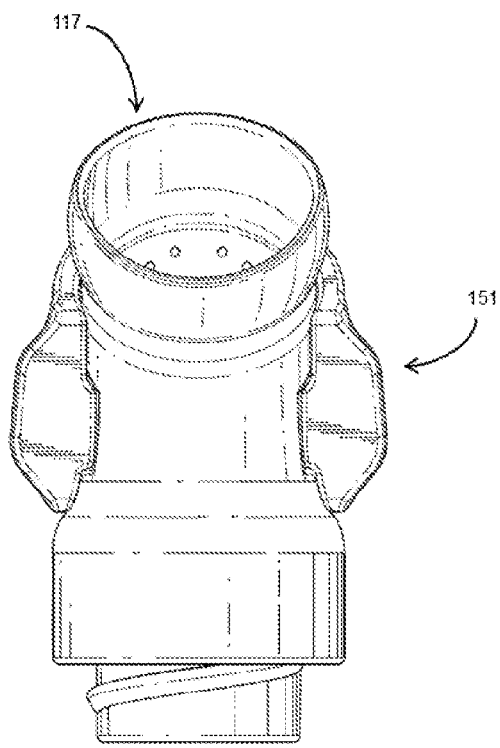
Figure 10E:
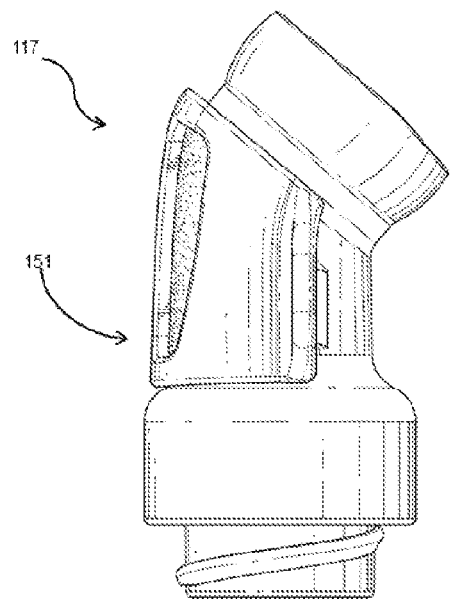

FIG. 7 is a side view of the respiratory mask 1 in use on a user U. It can be seen that, in use, the front plane is at an angle when the user U is upright. The angle of the posts 101 (noted above with reference to FIG. 6) is such that the retaining force F applied by the headgear 13 is substantially perpendicular to the angle of the post 101. This minimizes torsional forces between the headgear 13 and the mask frame 5, and thus improves the stability of the respiratory mask 1 on the user U. The lateral arms 97 are angled upwards such they extend along a direction extending from the ends of the lateral arms 97 to an area between the user's temples and ears.

In other words, the lateral or side arms 97 have a 3-D curvature. In use, the lateral arms 97 extend: outwardly from the center of the frame 5, rearwardly, towards the patients ears, and upwardly, along a vector passing from below the nose to a point between the temple the top of the ear. Additionally, the lateral arms 97 "twist" along their length, such that bottom corners of the ends of the lateral arms 97 are positioned further away from the central vertical plane than the top corners, for example, as shown in FIG. 5.

The positioning of the lateral arms 97 on the lower half of the mask frame 5 provides improved stability of the respiratory mask on the user's face. The retaining forces F applied by the headgear 13 to the mask frame 5 and sealing cushion 3 are predominantly applied through the lateral portions of the sealing cushion 3. This results in the retaining forces being applied predominantly to the lower surfaces of the user's nose, their upper lip and cheeks. This provides a greater surface area over which the forces can be spread and thus greater stability. The spreading of the forces over a greater surface area may also minimize any pressure points on the user's face, which may cause discomfort. If the lateral arms 97 were located higher on the mask frame 5 the force vector F would be predominantly applied to the tip of the user's nose, which may provide reduced stability to the respiratory mask 1. This may also cause discomfort to the user in the form of a pressure point on the tip of their nose.

The lower positioning of the lateral arms 97 provides the respiratory mask 1 with a more minimal appearance. Since the mask frame 5 is substantially positioned below the nose, in use, it is less visible and thus less dominating on the user's face. The lower positioning of the lateral arms 97 in combination with the angle of the post 99 also results in the headgear 13 passing over the user's cheek at a greater distance below the eyes. This is beneficial in that the headgear 13 is less likely to fall within the user's peripheral vision, making the mask 1 less obtrusive and more comfortable to wear.

Elbow and Diffuser

Shown in FIGS. 8 and 8A-8F is an elbow 117 similar to the elbow 17 described above, and configured to connect to the elbow connection aperture 77 (see e.g., FIGS. 1 and 3a). The elbow 117 includes a ball joint section 121 and a wide bottom portion 123. An elongate tube section 125 connects the ball joint section 121 and the wide bottom portion 123. The elongate tube section 125 is narrower than the wide bottom portion 123 and a largest diameter of the ball joint section 121. The elongated tube section 125 includes a long front section 127 (facing away from the user and mask, in use) and a short rear section 129 (facing towards the user and mask frame 5, in use). The elongated tube section 125 forms a truncated top 131 where the long front section 127 and short rear section 129 connect to the ball joint section 121. In this configuration, the elongate tube section 125 generally forms an elbow having an angle Ø.

The long front section 127 of the elongate tube section 125 includes a plurality of bias flow holes 135 for CO2 washout during use. The plurality of bias flow holes 135 is arranged in columns along a length of the long front section 127. In particular, as shown, the plurality of bias flow holes 135 is arranged in two sections or areas of two columns with a space between the two sections or areas of the elongate tube section 125. The columns within each section or area are offset, such that the bias flow holes of each row are nested with respect to each other, that is, the bias flow holes of one column are nested at least partially within the spaces between the bias flow holes of another column. The elongated tube section 125 further includes side sections 137, each having a notch 139. The notches 139 are configured to receive a part of a diffuser body having corresponding geometry.

The wide bottom portion 123 is short tube section that is concentrically offset from a conduit receiving section 141, such that an annular channel 143 is formed between the two. The conduit receiving section 141 is configured to receive the flexible gas supply conduit 9 on its outer surfaces. The annular channel 143 is configured to receive and retain the end of the flexible gas supply conduit 9. The conduit 9 receiving section includes a retaining formation which may be a projection and which is in this example is a screw thread 145, which is configured to retain the flexible gas supply conduit 9. The wide bottom portion 123 is configured to hide the end of the flexible gas supply conduit 9. Thus, the end of the flexible conduit 9 is threaded onto the elbow 117 to retain the conduit 9 on the elbow 117.

Shown in FIGS. 9A-D is a diffuser 151 configured to connect to the elbow 117, covering the bias flow holes 135 such that gas exhausted from the bias flow holes 135 passes through the diffuser 151. The diffuser 151 comprises a diffuser body 153 and a region or regions of a diffuser material 155. The diffuser body 153 comprises a substantially rigid plastic component having two lateral sides 157 and a front region 159 there between. The diffuser body 153 is configured to have a curvature that compliments the curvature of the elongate tube section 125 of the elbow 117, extending from one side section across the long front section to the other side section. The diffuser body 153 further comprises one or more diffuser openings 161 and a pair of grip tabs 163. The diffuser openings 161 are located in the front region 159 such that they overlap the bias flow holes 135, in use. In this example embodiment of the present disclosure the diffuser openings 161 are separated by a grill member 165.

The grip tabs 163 extend approximately perpendicularly from the edges of each of the lateral sides 157 of the diffuser body 153, and have a substantially trapezoidal profile. They are configured to allow the diffuser 151 to be gripped between the thumb and index finger of a user, during removal of the diffuser 151 from the elbow 117.

The diffuser body 153 has an internal surface 167, which is configured to be proximal to the elongate tube section 125 of the elbow 117, in use. The internal surface 167 comprises a pair of engagement tabs 169. The engagement tabs 169 extend inwardly from each of the grip tabs 163, and are configured to engage with the notches 139 of the elbow 117, such that the diffuser 151 is retained on the elbow 117.

The regions of diffuser material 155 are configured to fill the diffuser openings 161, providing a torturous path for exhaled air to pass through. The diffuser material 155 can be any breathable or porous material. In use, the diffuser material 155 is flush with the bias flow holes 135, thus ensuring that air venting out of the bias flow holes 135 is diffused through the diffuser material 155.

FIGS. 10A-10D show the elbow 117 and diffuser 151, wherein the diffuser 151 is connected to the elbow 117 such that the bias flow holes 135 are covered. It can be seen that, due to the narrow elongate tube section 125 of the elbow 117, the diffuser 151 may now be configured to have a width that is substantially equal to the outer diameter of the wide bottom section 123 of the elbow 117. Additionally, the elongate tube section 125 of the elbow 117 allows for longer columns of bias flow holes 135, and thus allows the elbow 117, and therefore the elbow 117 and diffuser 151 to be narrower. This affords the elbow 117 and diffuser 151 assembly a smaller and less bulky appearance.

Headgear

As shown in FIGS. 1 and 7 the respiratory mask 1 is secured in place on a user's head by a headgear 13. The headgear 13 comprises a three part construction, wherein the three parts include a pair of side straps 171 and a rear portion 173. The side straps 171 are configured to join to the rear portion 173 at one end and be connected to a headgear clip 175 at the other end. The side straps 171 can be joined to the rear portion 173 by any suitable means including but not limited to ultrasonic welding, radiofrequency welding, adhesive(s) or sewing. The end of the side strap 171 that connects to the headgear clip 175 comprises a securement tab 177 for adjustment of the headgear size. The securement tab 177 comprises the hook element of a hook and loop connector such as but not limited to Velcro™. The securement tab 177 is configured to attach to the outer surface of the side strap 171 in order to secure the length of the side strap 171, and thus the size of the headgear 13. The rear portion 173 comprises a bifurcated component having an upper and lower strap 173a, 173b, configured to engage a user's head in the occipital region. The headgear 13 can be made from any suitable non-stretch or stretch material known in the art, including but not limited to Neoprene, TPE, Breathoprene™ or knitted fabric, or any combination of materials. In a preferred embodiment the rear portion 173 and side straps 171 are made from a single material in contrasting colours. In alternative embodiments the rear portion 173 can be made from a different material to the side straps 171. In a further alternative embodiment the rear portion 173 and side straps 171 can be a single colour.

Closed Loop Headgear

Figure 11A:
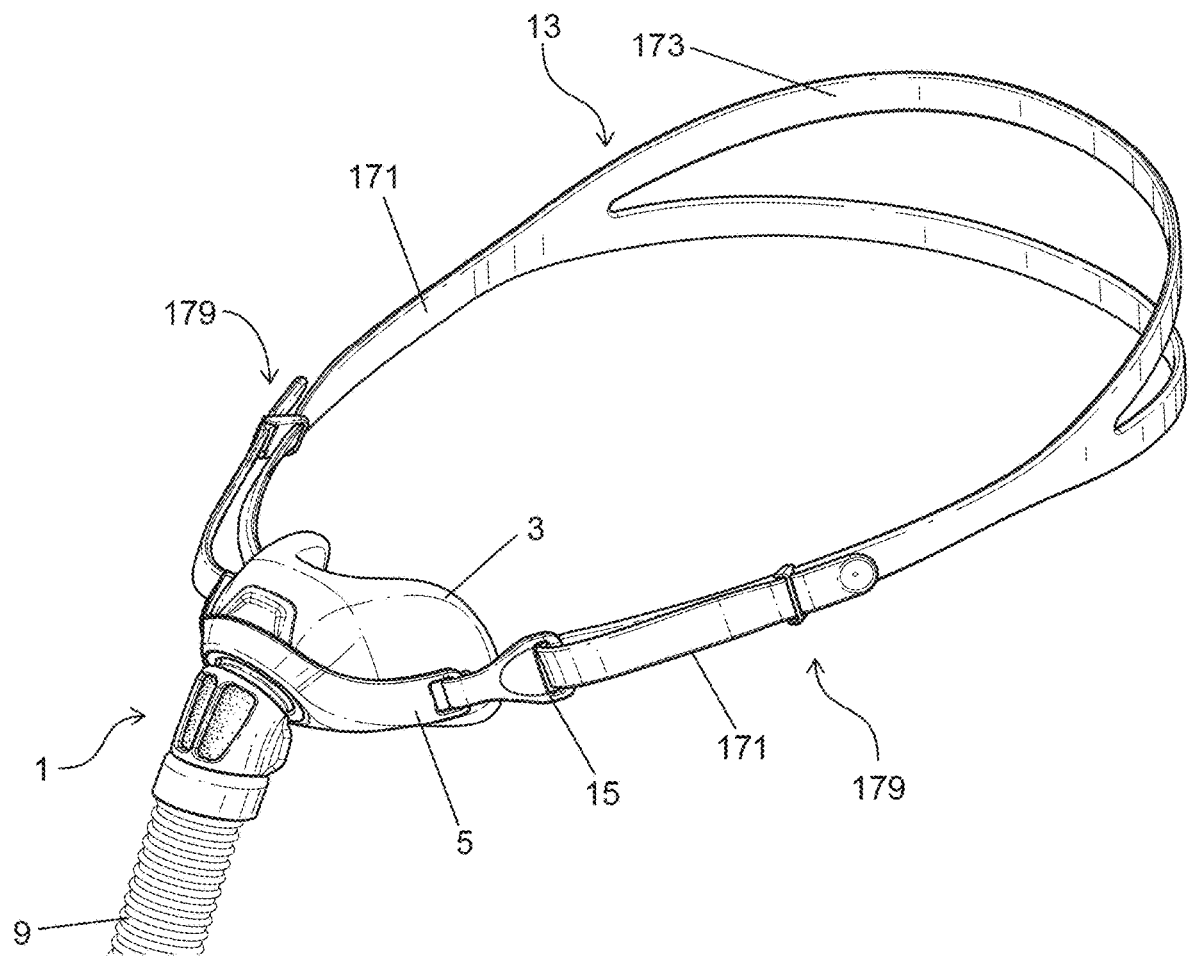
FIGS. 11A-11B show a non-limiting exemplary embodiment of a mask assembly with a closed loop headgear.
Figure 11B:
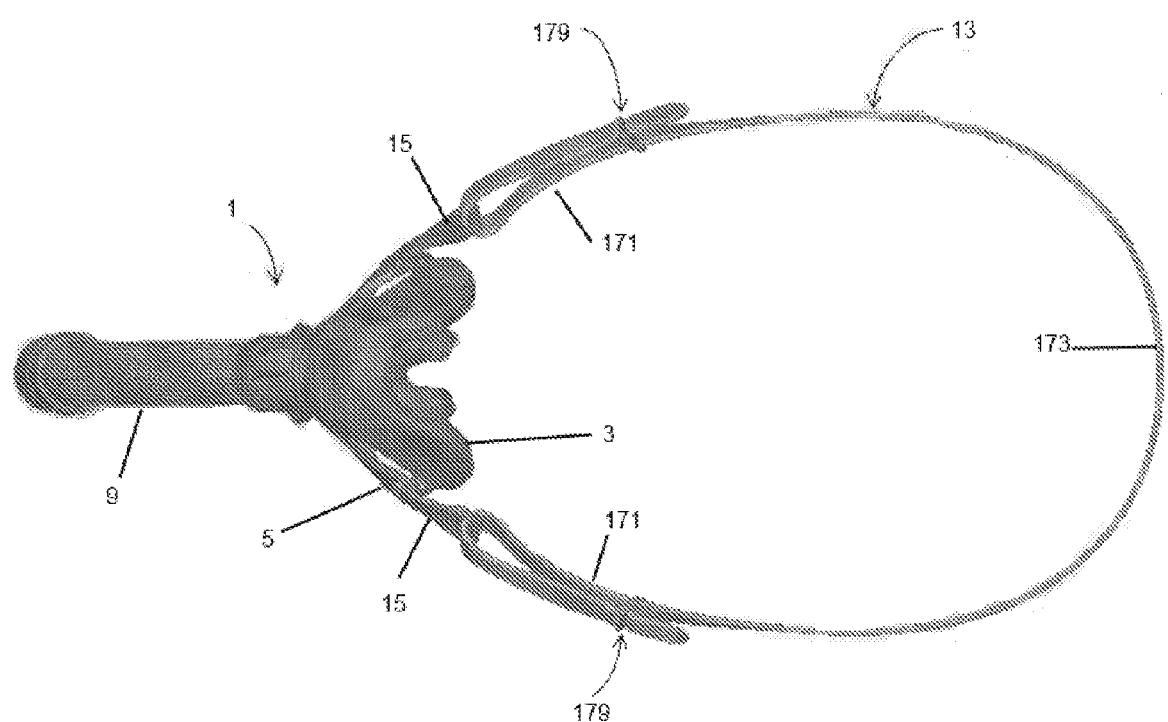

FIGS. 11A-11B show perspective and top views, respectively, of a non-limiting exemplary embodiment of a mask assembly 1 with a closed loop headgear 13. The mask assembly 1 is attached to a bifurcated headgear 13. Forward straps 171 extend forward from a rear, bifurcated section 173. The forward straps 171 pass through a buckle 179 then pass through a hook 101 which is attached to the mask assembly 1. Each forward strap 171 is doubled back, passing through the buckle 179.

The headgear 13 shown in FIGS. 11A-11B is a closed loop headgear, meaning that the length of the headgear can be adjusted from minimum length to a maximum length, but cannot be fully disassembled. A closed loop configuration may be desirable because the headgear 13 cannot be disassembled, and thus cannot be re-assembled incorrectly. The headgear 13 can be made from any suitable non-stretch or stretch material known in the art, including but not limited to Neoprene, TPE, Breathoprene™ or knitted fabric.

Figure 12A:
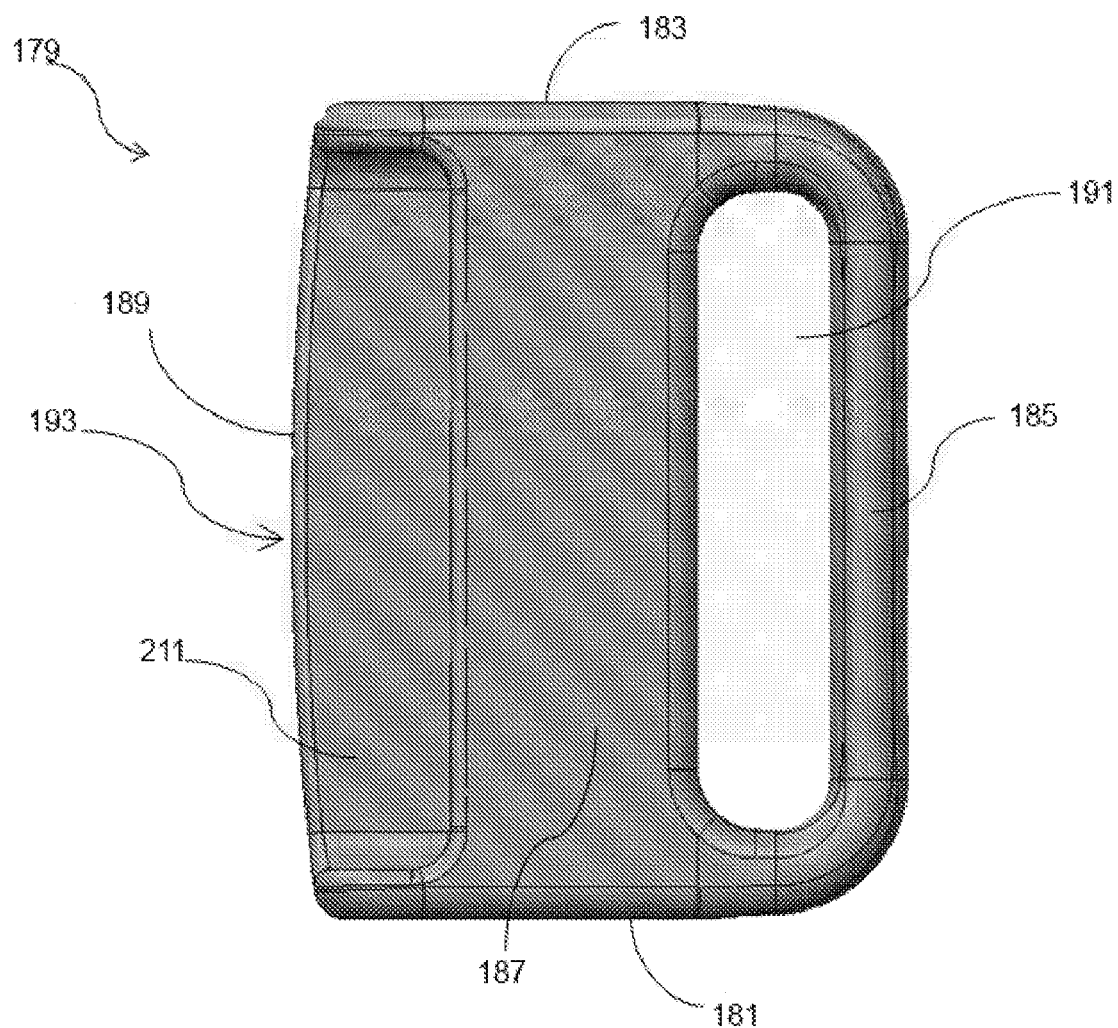
FIGS. 12A-12F show a non-limiting exemplary embodiment of a buckle for use in a closed loop headgear.
Figure 12B:
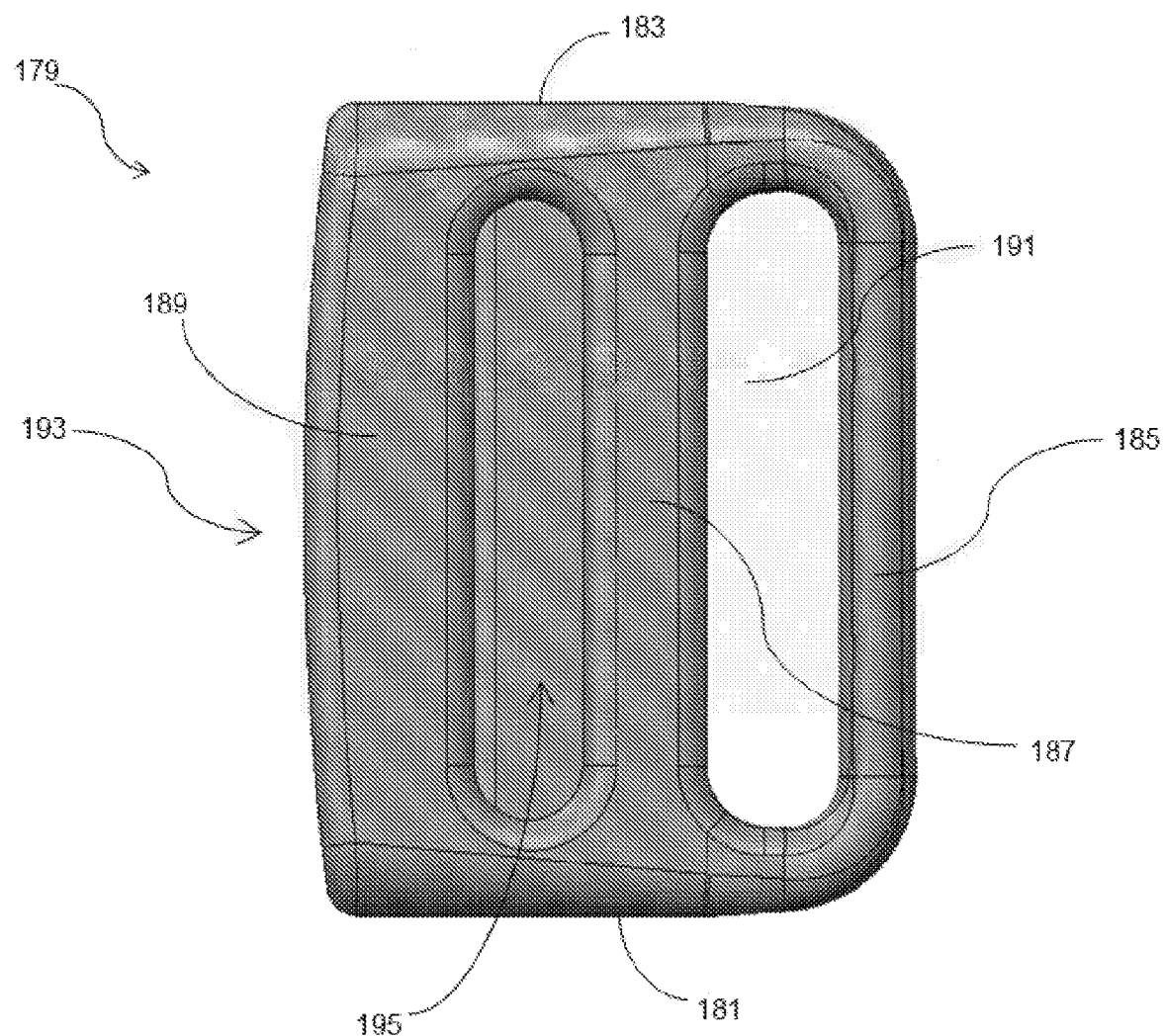

FIGS. 12A-12F show a non-limiting exemplary embodiment of a buckle 179 for use in a closed loop headgear 13, such as shown in FIGS. 11A-11B. FIGS. 12A-12B show and in an inside view and an outside view, respectively, of the buckle 179. As shown, the buckle 179 includes a bottom face 181 and a top face 183. Extending between the top and bottom sides 181, 183 are an inside post 185, a central post 187, and an outside post 189. Between the inside post 185 and the central post 187 is a friction loop opening 191. Between the outside post 189 and the central post 187 is a path comprising a front opening 193 and an outside opening 195. The front opening 193 and the outside opening 195 are offset, forming an angled path. Additionally, there is a strap attachment surface 197 located on an inside of the outside post 189.

Figure 12C:
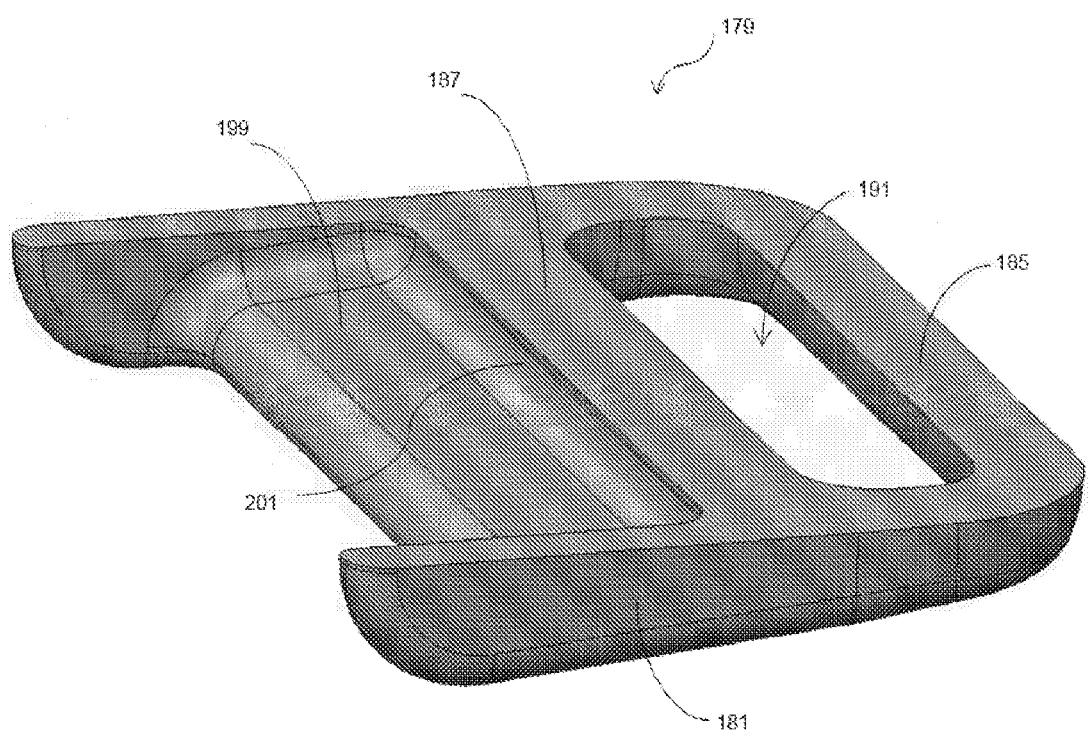
Figure 12D:
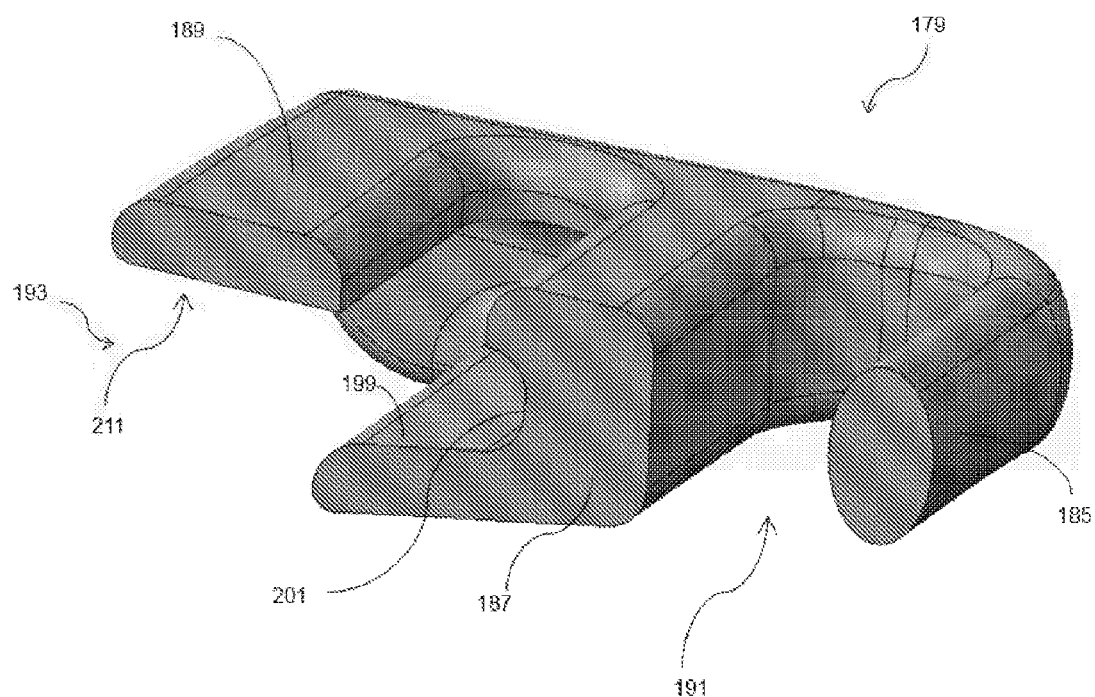

Shown in FIGS. 12C-12D are perspective cross-sections of the buckle 179, in particular to show internal features. On the central post 187 is a central post shoulder 199 and a central post recess 201.

Figure 12E:
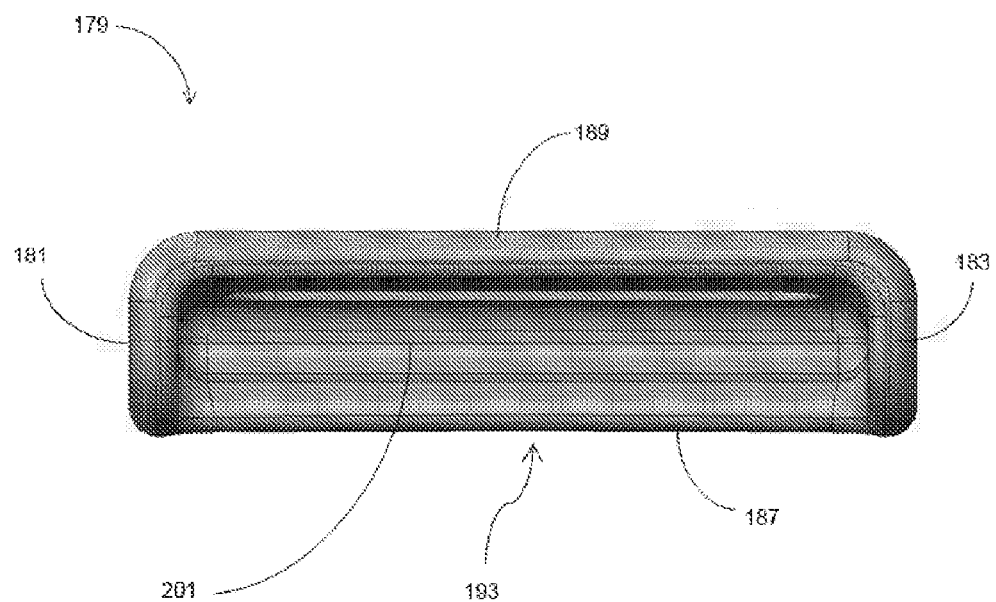
Figure 12F:
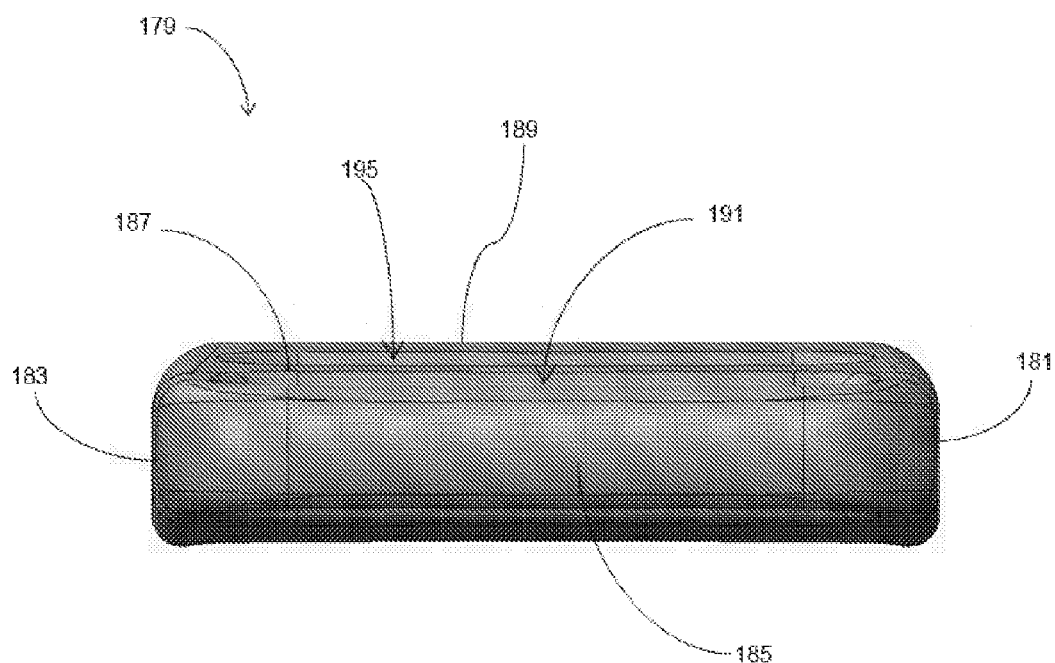

Shown in FIGS. 12E-12F are front and back views, respectively of the buckle, in particular to show additional views of the above described features.

Figure 13A:
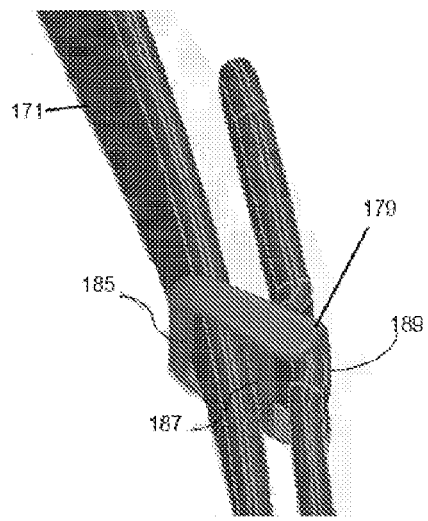
FIGS. 13A-13B are external perspective views of the buckle and strap used in the closed loop headgear.
Figure 13B:
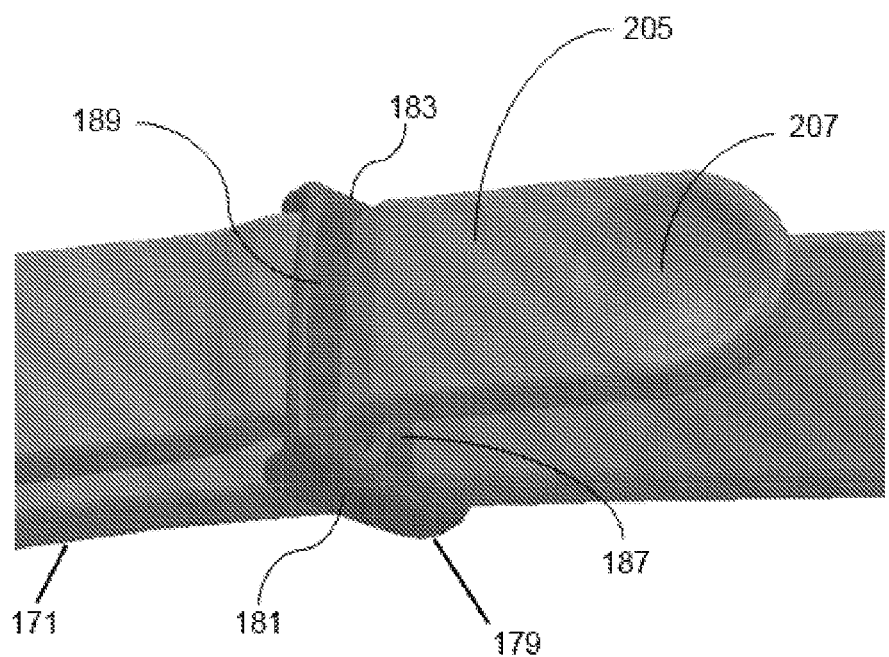

FIGS. 13A-13B are external perspective views of the buckle 179 and strap 171 used in the closed loop headgear 13. As shown, the strap 171 extending forward from the rear section 173 passes through the buckle 179 between the inside post 185 and the central post 187. The strap 171 continues, passing through the hook (see e.g., 11A) and doubles back, passing back through the central post 187 and outside post 189 of the buckle 179. The strap 171 includes a grip strap end 205 that extends through the buckle 179. The grip strap end 205 has a length long enough to grasp between a thumb and one or two fingers. A dimple 207 is provided for additional grip.

Figure 14A:
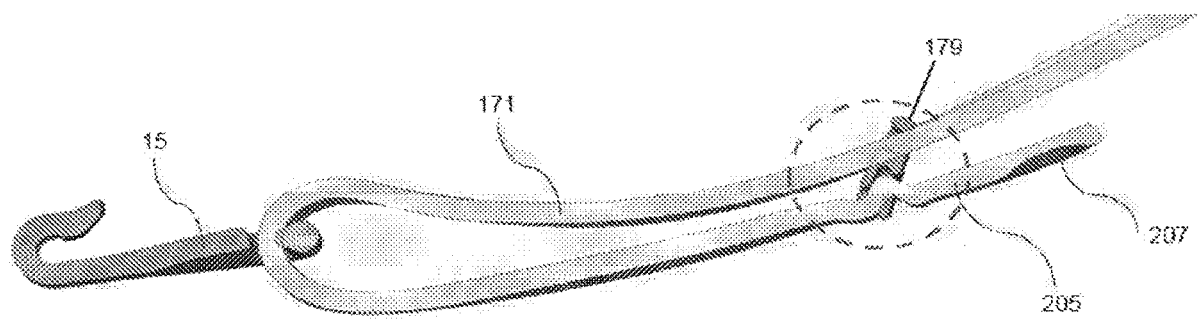
FIGS. 14A-14B the headgear strap passes through the buckle in cross-section.
Figure 14B:
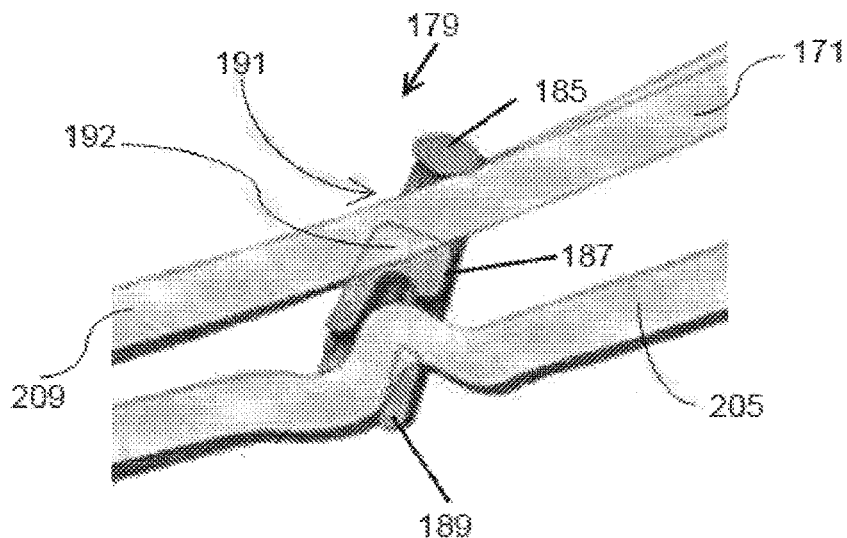

FIGS. 14A-B show a cross-section of the strap 171 passing through the buckle 179, forming an adjustable closed loop 209. The strap 171 passes through the friction loop opening 191 formed between the inside post 185 and the central post 187. The strap 171 passes back through the buckle 179, through the angled path formed between the front opening 193 to the outside opening 195.

As shown, the buckle 179 is relatively angled with respect to the strap 171. As a result of the angle in which the strap 171 passes through the friction loop opening 191, there is an interference corner 192 that generates a friction force that restricts the strap 171 from sliding though when under a tension. In particular, the plane of the strap 171 where the strap 171 passes through the friction loop opening is inclined relative to the plane of the buckle 179 so that the strap 171 is neither perpendicular nor parallel to the buckle 179.

The strap 171 is permanently attached to the buckle 179 at a strap attachment surface 211 located on an inside of the outside post 189 (see e.g., FIG. 12A). Because the strap 171 is permanently attached to the buckle 179, the headgear 13 cannot be disassembled (i.e., the hooks on the adjustable closed loop cannot be removed). The strap 171 may be attached to the strap attachment surface 211 by any suitable means including but not limited to ultrasonic welding, radiofrequency welding, adhesive(s) or sewing.

Figure 15A:
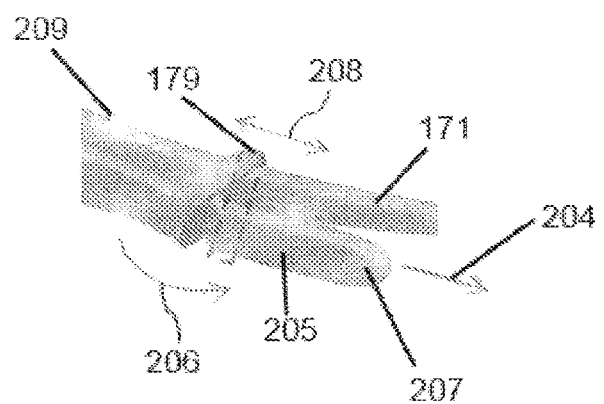
FIGS. 15A-15B show the closed loop headgear in sliding and friction modes.
Figure 15B:
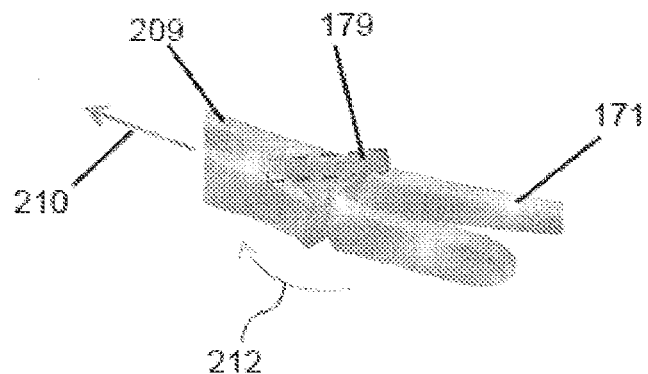
Figure 16A:
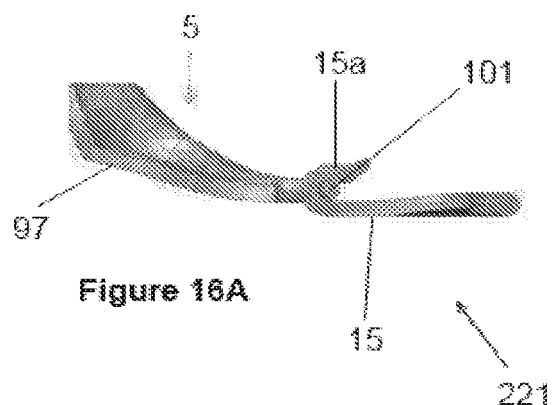
FIGS. 16A-16F show a non-limiting exemplary embodiment of a headgear connector assembly for connecting a headgear to a mask.
Figure 16B:
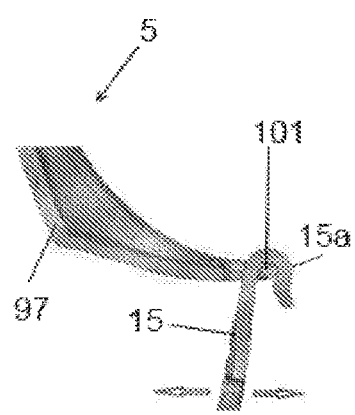
Figure 16C:
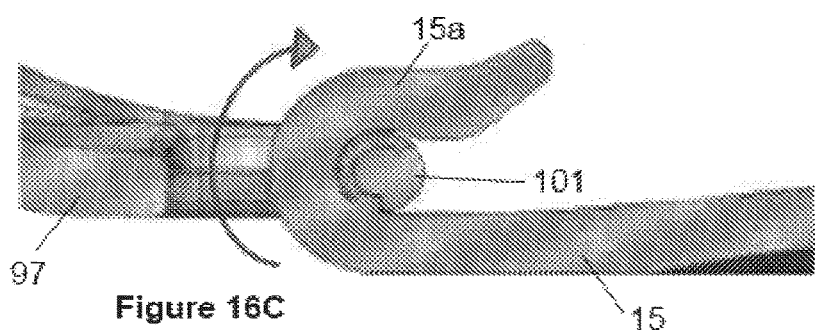
Figure 16D:
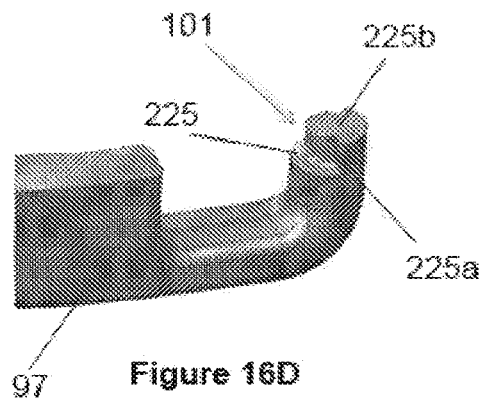
Figure 16E:
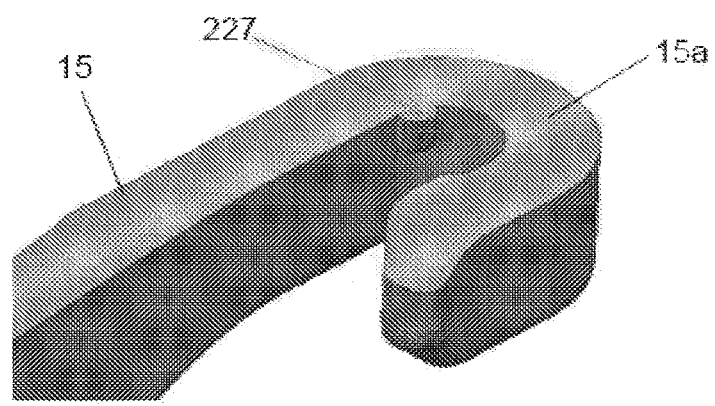
Figure 16F:
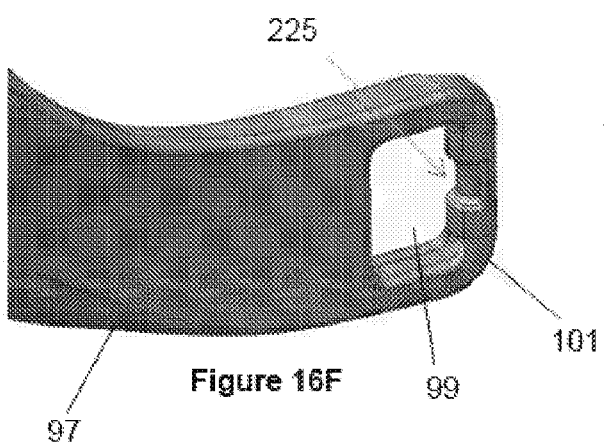

FIGS. 15A-B show the closed loop headgear 13 in sliding and friction modes, respectively. In FIG. 15A a pull force 204 is applied to the grip strap end 205. This pull force causes the buckle 179 to rotate 206 in the direction of the pull force (counter clockwise as shown). The "rotated" buckle 179 is represented in FIG. 15A as a dashed rectangle. The buckle 179 rotates with the pull force because the strap 171 is attached to the buckle 179 at the strap attachment surface 211. As the buckle 179 rotates, the buckle 179, in particular the friction loop opening 191 becomes more perpendicular with the strap 171 sliding 208 through the opening 191. As a result, the interference at the interference corner 192 (see e.g., FIG. 14B), and therefore friction force, is decreased. This allows the strap 171 to pass freely (or at least with less resistance) through the friction loop opening 191, thus allowing for adjustment.

Alternatively, as shown in FIG. 15B, a tension force 210 is applied, for example, when the mask assembly 1 is in use. The tension force 210 causes the buckle 179 to rotate 202 in the direction of the tension force (clockwise as shown). As the buckle 179 rotates, the buckle, in particular, the friction loop opening 191 becomes more angled with respect to the strap 171 passing through the opening 191. The "rotated" buckle 179 is represented in FIG. 15B as a dashed rectangle. As a result, the interference at the interference corner (see e.g., FIG. 14B) increases, and therefore the friction force between the friction loop opening 191 and the strap 171 passing through, increases.

Headgear Connector Assembly

With reference to FIGS. 16A-16F, headgear 13 be connected to the mask frame 5 using a hook and post type headgear connector assembly 221. In one example, the mask frame 5 comprises a post 101 on each lateral arm 97. Each headgear clip 15 comprises a hook 15a configured to receive a respective post 101 of the mask frame 5, to connect the headgear 13 to the mask frame 5.

In one embodiment, each headgear clip 15 is able to rotate freely about the respective post 101 on the mask frame 5. The post 101 is orientated generally vertically in normal use of the mask 1 and headgear 13, and the side straps 171 therefore rotate laterally about a generally vertical pivot axis. This can have the effect that prior to the mask 1 and headgear 13 being placed on the head of the user, the side straps 171 of the headgear 13 have pivoted around the posts 101 on the mask frame 5 to a position where part of the headgear 13 is adjacent the mask 1 and therefore impedes the mask 1 being located on the face of the user. The side straps 171 of the headgear 13 may therefore rotate around the posts 101 of the mask frame 5 such that the side straps 171 impede the internal side of the seal body 53. This can make the mask 1 and headgear 13 difficult or inconvenient to put on.

It may be desirable to be able to prevent, limit or control the extent of relative rotational movement between the headgear 13 and the mask frame 5, and particularly, to limit the extent of rotation of the side straps 171 of the headgear 13 relative to the mask frame 5.

With further reference to FIGS. 16A-16F, in one embodiment, the post 101 of the mask frame 5 and the hook 15a of the headgear clip 15 each comprise a respective movement limiting formation. These formations are arranged to engage to prevent, or at least limit the extent of, relative rotational movement between the mask frame 5 and the headgear 13, and more particularly, between the mask frame 5 and the side straps 171 of the headgear 13. The headgear connector assembly 221 between the mask 1 and headgear 13 therefore performs a rotation limiting function, to help prevent the side straps 171 of the headgear 13 rotating relative to the mask frame 5 to a position where they impede the mask 1, and particularly the internal side of the seal body 53.

In one embodiment each post 101 of the mask frame 5 comprises a recessed region, of reduced diameter as compared to the remainder of the post 101, which forms a groove or recess 225 extending partially around the post 101, in a plane perpendicular to the axis of the post 101. When viewed from above, that is, along the axis of the post 101, the groove or recess 225 extends around only a portion of the post 101, that is, the groove or recess 225 is part circumferential. The groove or recess 225 may extend through about 180° for example. The groove or recess 225 thus comprises two opposed ends 225a, 225b where the groove or recess 225 meets the non-recessed part of the post 101. These ends 225a, 225b are movement limiting formations comprising end stops.

Each hook 15a also comprises a movement limiting feature which in one example comprises a bump or protrusion 227 on the inside face of the hook 15a which functions as an end stop, that is, on the part of the hook 15a which receives the post 101 in use. When the post 101 is received in the hook 15a, which may be using a snap-fit type connection, relative rotation may occur between the post 101 and hook 15a with the bump 227 of the hook 15a moving within the groove or recess 225. This allows the side straps 171 of the headgear 13 to pivot about the post 101 of the mask frame 5 to a limited extent. When a side strap 171 has rotated a predetermined distance relative to the mask frame 5, the bump 227 reaches one end of the groove or recess 225 and abuts a groove or recess end stop 225a, 225b, this abutment preventing further relative rotation between the hook 15a and post 101. The bump 227 can thus travel a predetermined distance along the groove or recess 225 before further movement of the hump 227, and therefore rotation of the side strap 171 relative to the mask frame 5, is prevented.

It will be appreciated that in another embodiment, the hook 15a and post 101 could be reversed, with the hook 15a being provided on the mask frame 5 and the post 101 being provided on the headgear clip 15. Likewise, it is envisaged that the bump or protrusion 227 could be formed on the post 101, and the groove or recess 225 on the hook 15a.

The groove or recess 225 may be provided at any location along the length of the post 101, that is, at any axial position on the post 101. More than one groove or recess 225 and bump 227 may be provided. The length of the groove or recess 225 and/or the size of the bump 227 may be selected to achieve the desired degree of relative rotation between the post 101 and hook 15a.

In at least one embodiment, the groove or recess 225 is positioned on a left side post 101 at a first vertical spacing and the groove or recess 227 is positioned on a right side at a second vertical spacing. In some embodiments the first and second vertical spacing are different. The corresponding left and right hooks 15a include a protrusion 225, the protrusion 225 being at the first vertical height and the second vertical height such that the left and right hooks 15a are connectable to one of the left side post 101 or the right side post 101.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The inventions disclosed herein may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the inventions and without diminishing its attendant advantages. For instance, various components may be repositioned as desired. It is therefore intended that such changes and modifications be included within the scope of the inventions. Moreover, not all of the features, aspects and advantages are necessarily required to practice the present inventions. Accordingly, the scope of at least some of the present inventions is intended to be defined only by the claims that follow.

What is claimed is:

1. A mask frame for a patient mask for delivering breathing gases to a patient, the mask frame comprising:
   a central region comprising a conduit connection aperture configured to be connected to a breathing gas delivery conduit, a notional central vertical plane extending through a centre of the conduit connection aperture; and
   first and second lateral arms each extending outwardly from the central region away from the notional central vertical plane;
   wherein each of the first and second lateral arms having a length and terminating in a distal end remote from the central region, each of the first and second lateral arms comprising top and bottom margins;
   wherein each of the first and second lateral arms twists along its length such that the bottom margin at the end of each of the first and second lateral arms is positioned further away from the notional central vertical plane than the top margin at the end of each of the first and second lateral arms;
   a planar surface extending radially outward from the conduit connection aperture, wherein the notional central vertical plane extends perpendicular to the planar surface, wherein the ends of each of the first and second lateral arms are positioned below a notional horizontal mid plane that passes through the centre of the conduit connection aperture, the notional horizontal mid plane perpendicular to the planar surface and the notional central vertical plane.

2. The mask frame of claim 1, wherein each of the first and second lateral arms extend:
   laterally outwardly from the central region of the mask frame;
   rearwardly, towards ears of the patient; and
   upwardly, so that each of the first and second lateral arms are angled upwards such that they extend along a direction extending from the ends of each of the first and second lateral arms to an area between temples of the patient and the ears of the patient.

3. The mask frame of claim 2, wherein each of the first and second lateral arms extend upwardly along a vector passing from below a nose to a point between one of the temples and a top of one of the ears.

4. The mask frame of claim 1, wherein each of the first and second lateral arms comprises a planar strip, the end of each planar strip defining top and bottom corners at the top and bottom margins respectively, wherein the each of the first and second lateral arms twist along their length such that the bottom corner of the ends of each of the first and second lateral arms are positioned further away from the central region of the mask frame than the top corners.

5. The mask frame of claim 4, wherein each of the first and second lateral arms is tapered along its length, wherein a distance between the top and bottom margins reduces along at least part of the length of each of the first and second lateral arms.

6. The mask frame of claim 1, wherein the end of each of the first and second lateral arms comprises a headgear connector configured to connect the mask frame to a headgear.

7. The mask frame of claim 6, wherein the headgear connector comprises a loop and a post configured to provide a connection point for a hook of a headgear clip attached to the headgear.

8. The mask frame of claim 6, wherein the headgear connector comprises a rotation limiting formation configured to limit relative rotation between the headgear connected to the headgear connector, and the mask frame.

9. The mask frame of claim 8, wherein the rotation limiting formation comprises an end stop against which the headgear abuts after a predetermined amount of relative rotation between the mask frame and the headgear.

10. The mask frame of claim 1, wherein a distal side the central region comprises a planar surface extending radially outwardly from the connection aperture.

11. The mask frame of claim 10, further comprising a notional front plane coincident with the planar surface, wherein the bottom margin of each of the first and second lateral arms are closer to the notional front plane than the top margin of each of the first and second lateral arms.

12. The mask frame of claim 11, wherein the ends of each of the first and second lateral arms comprises a post, wherein each of the posts form an acute angle with the notional front plane.

13. The mask frame of claim 1, wherein a proximal side of the central region comprises an annular wall that projects in a rearward direction around a perimeter of the connection aperture.

14. The mask frame of claim 13, wherein an internal surface of the annular wall comprises a concave spherical section.

15. The mask frame of claim 13, wherein an external surface of the annular wall comprises one or more indentations configured to be coupled to corresponding geometry on a mask frame connector.

* * * * *